United States Patent
Mendolia et al.

[11] Patent Number: 5,919,441
[45] Date of Patent: Jul. 6, 1999

[54] COSMETIC COMPOSITION CONTAINING THICKENING AGENT OF SILOXANE POLYMER WITH HYDROGEN-BONDING GROUPS

[75] Inventors: Michael S. Mendolia, Bridgewater; Paul J. Vincenti, Jefferson; Morton L. Barr, East Brunswick; Anthony Esposito, Roselle, all of N.J.; Yigal Blum, San Jose, Calif.; Hans-Werner Schmidt, Bayreuth, Germany; Huiyong Paul Chen, Sunnyvale, Calif.; Gisbert Riess, Munchberg, Germany; Hui-Jung Wu, Fremont, Calif.

[73] Assignee: Colgate-Palmolive Company, New York, N.Y.

[21] Appl. No.: 08/790,351

[22] Filed: Jan. 24, 1997

Related U.S. Application Data

[60] Provisional application No. 60/025,595, Sep. 6, 1996, and provisional application No. 60/014,515, Apr. 1, 1996.

[51] Int. Cl.$^6$ ..................................................... A61K 31/74
[52] U.S. Cl. .......................... 424/78.08; 424/401; 424/65; 424/66; 424/67; 424/68; 424/59; 424/60; 514/844; 514/845; 514/846; 514/847; 514/848; 514/873; 514/880; 514/881; 514/944
[58] Field of Search .................. 424/59, 60, 65, 424/66, 67, 68, 70.6, 70.7, 70.11, 70.12, 70.121, 70.122, 401, 78.08; 514/63, 844, 845, 846, 847, 848, 873, 880, 881, 944

[56] References Cited

U.S. PATENT DOCUMENTS

| | | | |
|---|---|---|---|
| 2,900,306 | 8/1959 | Slater .......................................... 424/65 |
| 3,148,125 | 9/1964 | Strianse et al. ............................ 424/64 |
| 3,255,082 | 6/1966 | Barton ........................................ 424/68 |
| 3,288,754 | 11/1966 | Green ......................................... 528/26 |
| 3,341,501 | 9/1967 | Hedrick et al. .......................... 528/320 |
| 3,457,323 | 7/1969 | Stengle ..................................... 525/431 |
| 3,637,550 | 1/1972 | Sprauer .................................... 525/420 |
| 3,903,046 | 9/1975 | Greber et al. ............................ 525/431 |
| 3,948,835 | 4/1976 | Greber et al. ............................ 525/431 |
| 4,049,792 | 9/1977 | Elsnau ........................................ 424/66 |
| 4,137,306 | 1/1979 | Rubino et al. ............................. 424/68 |
| 4,279,658 | 7/1981 | Harvey et al. ......................... 106/217.2 |
| 4,346,079 | 8/1982 | Roehl ......................................... 424/65 |
| 4,429,082 | 1/1984 | Lee et al. ................................. 525/426 |
| 4,647,630 | 3/1987 | Schmid et al. ........................... 525/431 |
| 4,673,570 | 6/1987 | Soldati ....................................... 424/66 |
| 4,675,367 | 6/1987 | Policastro et al. ....................... 525/474 |
| 4,783,511 | 11/1988 | Schmid .................................... 525/431 |
| 4,806,338 | 2/1989 | Smith . |
| 4,853,214 | 8/1989 | Orr ............................................ 424/69 |
| 4,937,069 | 6/1990 | Shin .......................................... 424/66 |
| 4,962,178 | 10/1990 | Harisiades ................................ 528/33 |
| 4,972,037 | 11/1990 | Garbe et al. ............................. 526/245 |

(List continued on next page.)

FOREIGN PATENT DOCUMENTS

| | | |
|---|---|---|
| 291334 A2 | 11/1988 | European Pat. Off. . |
| 636361 | 2/1995 | European Pat. Off. . |
| 0 738 511 A1 | 10/1996 | European Pat. Off. . |
| 0 751 162 A1 | 1/1997 | European Pat. Off. . |
| 2 299 024 | 3/1996 | United Kingdom . |
| WO 92/05767 | 4/1992 | WIPO . |
| WO 96/15171 | 5/1996 | WIPO . |
| WO 96/32918 | 10/1996 | WIPO . |

*Primary Examiner*—José G. Dees
*Assistant Examiner*—Michael A. Williamson
*Attorney, Agent, or Firm*—Rosemary M. Miano; William I. Solomon

[57] ABSTRACT

An invention is disclosed which comprises gelling agents which (1) contain both siloxane groups and hydrogen-bonding groups to thicken compositions containing silicone fluids (volatile and/or non-volatile silicone fluids); (2) are non-flowable solids at room temperature; and (3) dissolve in a fluid which contains silicone at a temperature of 25–250 degrees C to form a translucent or clear solution at a temperature in this range. Cosmetic compositions may be made by adding at least one active ingredient such as an antiperspirant.

81 Claims, 1 Drawing Sheet

U.S. PATENT DOCUMENTS

| | | | |
|---|---|---|---|
| 5,013,577 | 5/1991 | Wright et al. | 427/503 |
| 5,019,375 | 5/1991 | Tanner et al. | 424/66 |
| 5,069,897 | 12/1991 | Orr | 424/66 |
| 5,102,656 | 4/1992 | Kasat | 424/66 |
| 5,120,531 | 6/1992 | Wells et al. | 424/70.15 |
| 5,164,522 | 11/1992 | McCarthy et al. | 554/39 |
| 5,196,499 | 3/1993 | O'Lenick, Jr. | 528/15 |
| 5,209,924 | 5/1993 | Garbe et al. | 424/70.11 |
| 5,210,133 | 5/1993 | O'Lenick, Jr. | 525/54.1 |
| 5,221,724 | 6/1993 | Li et al. | 528/28 |
| 5,243,010 | 9/1993 | Choi et al. | 528/28 |
| 5,272,241 | 12/1993 | Lucarelli et al. | 528/15 |
| 5,306,838 | 4/1994 | Shioya et al. | 556/445 |
| 5,334,737 | 8/1994 | Thimineur et al. | 556/440 |
| 5,403,580 | 4/1995 | Bujanowski et al. | 424/65 |
| 5,449,729 | 9/1995 | Lai | 526/286 |
| 5,466,849 | 11/1995 | Shioya et al. | 424/401 |
| 5,500,209 | 3/1996 | Ross et al. | 424/66 |
| 5,603,925 | 2/1997 | Ross et al. | 424/65 |
| 5,632,974 | 5/1997 | Galleguillos et al. | 424/66 |

COSMETIC COMPOSITION CONTAINING THICKENING AGENT OF SILOXANE POLYMER WITH HYDROGEN-BONDING GROUPS

This application claims priority under 35 USC 119(e)(1) of provisional applications Ser. Nos. 60/025,595, filed Sep. 6, 1996 and 60/014,515, filed Apr. 1, 1996.

BACKGROUND OF THE INVENTION

The present invention is directed to a cosmetic composition (for example, a solid cosmetic composition, such as a gel, soft-solid or semi-solid (cream), or stick), comprised of a base composition containing at least one silicone fluid (for example, silicone liquids such as silicone oils) which is thickened using a gelling agent, which base composition can include increased amounts of the silicone fluids; a carrier in which cosmetically active materials are incorporated; and at least one active ingredient to provide the activity for such cosmetic composition. Particular embodiments of the present invention include deodorant and antiperspirant compositions (and base compositions therefor), in which the cosmetically active ingredient is a deodorant active material and/or an antiperspirant active material, which can include increased amounts of silicone fluids. The present invention is not limited, however to such antiperspirant and/or deodorant compositions, and is also directed to other cosmetic compositions containing other cosmetically active ingredients, such as sun protection compositions containing sun-screen agents as the active material. In particular, the present invention is directed to cosmetic compositions which are preferably transparent (clear), including solid transparent (clear) compositions, especially transparent (clear) deodorant and/or antiperspirant compositions, which can include increased amounts of silicone fluids. While the present compositions are preferably clear or transparent, the compositions need not, however, be clear or transparent, and can be translucent, or can be opaque.

The compounds used as gelling agents in this invention include selected siloxane polymers with hydrogen bonding groups, such as hydrogen bonding groups selected from the group comprising ester groups, urethane groups, urea groups, thiourea groups, amide groups and groups which have more than one of the aforementioned groups such as urea-urethane compounds.

Particular forms of the invention include clear or transparent antiperspirant compositions in stick or gel form. More particularly, such embodiments are directed to a clear gel or stick composition including a polyurea, polyurethane or polyamide gelling agent, and having an active ingredient (for example, an antiperspirant active material) incorporated therein, the composition having improved application and cosmetic properties (including reduced tackiness and stickiness).

Antiperspirant products are well known in the art. Antiperspirant products have appeared in the marketplace in various dosage forms, such as sticks, gels, roll-ons, aerosols and creams. Generally, these dosage forms include a solution of the active ingredient in a solvent, a suspension of the active ingredient in a non-solvent, or a multi phase dispersion or emulsion in which a solution of the active ingredient is dispersed in some continuous phase or in which the solubilized active ingredient constitutes a continuous phase.

Of the above-referred-to dosage forms, the roll-on is an example of a liquid form composition, the stick form is an example of a solid form composition, and the gel form is a thickened form which may or may not be a solid (for example, under some circumstances gels can flow). The stick form can be distinguished from a gel in that, in a stick, the formulated product can maintain its shape for extended time periods outside the package, the product not losing its shape significantly (allowing for some shrinkage due to solvent evaporation), while a gel cannot so maintain its shape. Adjustment of amounts of gelling or thickening agents such as bentones, fumed silica or polyethylene, or stearyl alcohol and castor wax, can be used in order to form a gel or stick.

Gels, pastes and creams (which are also known as soft-solids or semi-solids) can be suitably packaged in containers which have the appearance of a stick, but which dispense through apertures (for example, slots or pores) on the top surface of the package. These products have been called soft sticks or "smooth-ons". These products hereinafter are generically called "gels". Reference is made to U.S. Pat. No. 5,102,656 to Kasat, U.S. Pat. No. 5,069,897 to Orr, and U.S. Pat. No. 4,937,069 to Shin, each of which discloses such gels, including physical characteristics thereof such as viscosity and hardness. The contents of each of these three U.S. patents are incorporated herein by reference in their entirety.

A representative composition which can be dispensed through apertures is described in U.S. Pat. No. 5,102,656 to Kasat. This disclosed composition is a creamy, heterogeneous anhydrous antiperspirant product containing, in percent by weight, of the total weight of the composition, 30%–70% of a volatile silicone as a carrier, 7–30% of a suitable gelling agent or agents, and about 12–30% of a physiologically acceptable antiperspirant agent. This patent discloses that the gelling agent can be any of a number of materials, including, for example, hydrogenated vegetable oil, hydrogenated castor oil, fatty acids having from 14 to 36 carbon atoms, beeswax, paraffin wax, fatty alcohols having from 14 to 24 carbon atoms, polyethylene and the like.

Recently, there has been significant activity in developing clear or translucent antiperspirant sticks and gels. Clear or translucent sticks consisting essentially of a solution of the active antiperspirant material in a polyhydric alcohol vehicle, gelled by dibenzylidene monosorbitol acetal, have been disclosed. Since the gelling agent is inherently unstable in an acidic environment, and since conventional active antiperspirant materials are acidic, much work has been involved in discovering suitable stabilizing or buffering agents to prevent or slow down acid attack on the acetal gelling agent. Such work has not been completely successful. Moreover, these clear or translucent antiperspirant sticks containing the acetal gelling agent and including a solubilized active antiperspirant material, have the disadvantage of being inherently tacky. Thus, development work in connection with these clear or translucent antiperspirant sticks containing the acetal gelling agent has also focused on discovering suitable anti-tack agents for this dosage form. However, since acid hydrolysis of the gelling agent occurs more rapidly in aqueous solutions, formulators have been forced to avoid using water in the formulations. This severely restricts the ability of the formulator to develop cosmetically elegant formulations which are simultaneously chemically stable, optically clear, low in tack, low in residue and which have acceptable application aesthetics.

Clear or translucent antiperspirant gels (which have been dispensed from containers having the appearance of a stick) have been marketed, consisting of viscous, high internal phase emulsions. These gels exhibit some advantages over the aforementioned acetal-based clear sticks, in that the selection of formulation ingredients is less restricted (for example, water can be used), and often tack can be reduced significantly. But these emulsions suffer from various disadvantages, including often requiring the use of ethanol to achieve desired aesthetics. In addition, these emulsions are relatively expensive. In connection with these emulsions, see U.S. Pat. No. 4,673,570 to Soldati and PCT (International Application) Publication No. WO 92/05767, the contents of each of which are incorporated herein by reference in their entireties.

U.S. Pat. No. 5,403,580 to Bujanowski, et al discloses an antiperspirant product which is an organosilicon gel, containing as components at least one material selected from the group consisting of astringent antiperspirant compounds, a volatile silicone, a suspending agent, a waxy material, emollients, perfumes, coloring agents and other ingredients normally used in making antiperspirant products. This composition utilizes as a gelling agent an organic compound which includes polycyclic aromatic and steroidal groups linked through ester linkages. These gels are thermally irreversible. The gelling agent is predissolved in an organic solvent, among which are halogenated organic compounds such as chloroform, and gelation occurs by crystallization of the gelling agent from the silicone-solvent mixture. The contents of U.S. Pat. No. 5,403,580 are incorporated herein by reference in their entirety.

European Patent Application No. 636,361 to Mougin, et al discloses a cosmetic composition containing, in a cosmetic carrier, at least one pseudo-latex based on a multi-sequenced polycondensate having a chain formed by (a) at least one polysiloxane sequence, and (b) at least one polyurethane and/or polyurea sequence containing anionic or cationic components. This reference discloses cosmetic compositions which are specifically useful as hair-treatment compositions and make-up compositions.

U.S. Pat. No. 5,120,531 to Wells, et al discloses rinse-off hair conditioner compositions providing both hair conditioning and hair styling benefits. The described compositions include specific amounts of a hair conditioning agent, a hair styling polymer formed from specific monomers, a non-aqueous solvent solubilizing the polymer, and an aqueous carrier. This patent discloses that the conditioning agent can provide not only hair conditioning benefits but also provide a gel-network thickened vehicle for the styling polymer and solvent. This patent discloses various siloxanes as the conditioning agent including polydiorganosiloxanes having quaternary ammonium-substituted groups attached to the silicon, and polydiorganosiloxanes having silicone-bonded substituents which are amino-substituted hydrocarbon groups.

U.S. Pat. No. 5,500,209 (issued on Ser. No. 08/214,111), the contents of which are incorporated herein by reference in their entirety, discloses a gel or stick which includes active deodorant and/or antiperspirant ingredients, a polyamide gelling agent, and a solvent for the polyamide gelling agent, which gel or stick composition can be clear or translucent. This patent application discloses that the polyamide gelling agent is soluble in a cosmetically acceptable solvent at elevated temperatures, and solidifies (gels) upon cooling; acceptable solvents are disclosed as including various alcohols, including various glycols. While the polyamide-containing stick or gel disclosed in the aforementioned U.S. patent contains desirable properties in connection with stability of the composition, particularly in the presence of acidic antiperspirant active materials, and in providing clear or translucent gel or stick compositions, various attributes need to be improved. Specifically, the compositions according to U.S. Pat. No. 5,500,209 containing glycol solvents for the polyamide gelling agent and/or for the antiperspirant active material, may have a disadvantageously large amount of tackiness and stickiness both upon and after application to the skin.

Addressing this problem of tackiness and stickiness in connection with cosmetic compositions utilizing a polyamide gelling agent, U.S. patent application Ser. No. 08/426,672, filed Apr. 21, 1995, the contents of which are incorporated by reference herein in their entirety, discloses use of a specific solvent system for a solid composition containing an antiperspirant active material and a polyamide gelling agent. This solvent system is glycol-free and contains a non-ionic surfactant and a polar solvent. Water is the polar solvent, and with the non-ionic surfactant acts as a dispersing medium for the antiperspirant active material, in which sufficient water is used to give a clear or translucent solution/emulsion of the antiperspirant active material.

A typical technique to reduce the tackiness of, for example, antiperspirant formulations is the incorporation of cyclomethicone (a mixture of penta- and hexacyclodimethyl-siloxanes). This cyclomethicone is a very low-viscosity liquid that provides excellent lubricity, which eliminates the tacky feeling. Cyclomethicone is also mildly volatile and therefore does not leave stains on the skin and/or clothing. More than 50% by weight of cyclomethicone has been incorporated into solid stick antiperspirant formulations, for example, using a wax solidifying agent. However, cyclomethicone is a nonsolvent for the dimer based polyamides described as gelling agents in U.S. Pat. No. 5,500,209. Moreover, only limited quantities of the cyclomethicone (for example, 37% by weight) can be incorporated in solid compositions gelled using such polyamide gelling agent, without destroying the clarity of the gelled composition. Beyond that point, the gelled composition becomes cloudy because of either excessive crystallization of the polyamide or immiscibility of the cyclomethicone in the mixture.

U.S. Pat. No. 5,243,010 to Choi, et al., the contents of which are incorporated herein by reference in their entirety, discloses aromatic polyamide resins having pendant silyl groups, such resin having excellent heat-resistance, mechanical strength, electrical conductivity and other physical properties, as well as excellent solubility in common organic solvents and improved molten processing properties. This patent does not describe use of the aromatic polyamide resin as a gelling agent, much less as a gelling agent in cosmetic compositions to provide solid cosmetic compositions.

U.S. Pat. No. 5,272,241 to Lucarelli, et al., the contents of which are incorporated herein by reference in their entirety, discloses organofunctional siloxanes useful in both the personal care and plastics industries, the siloxanes being amino acid functionalized silicones. It is disclosed in this patent that the siloxanes have uses as plastic additives, hydraulic fluids, vibration damping agents, release agents, antifoamers, dielectric media, water repellents, surfactants, cosmetic and health product additives, lubricants, etc. This patent does not disclose use of the siloxanes as gelling agents.

Notwithstanding the foregoing, there is still a need for base compositions, thickened with a gelling agent, which base compositions can include increased amounts of silicone fluids (for example, silicone liquids, both volatile and non-volatile), and which base compositions are useful in forming cosmetic compositions. Such increased levels of silicone fluids are desired because these silicone fluids impart good cosmetic characteristics to the composition. Specifically, these fluids are desirable because of their skin feel, volatility and low toxicity. Moreover, it is also desired to provide such base compositions, thickened utilizing such gelling agent, which are transparent and clear, and can be formed into products having varying degrees of firmness, such as from a cream to a stick, depending on amounts of thickening agent contained in the composition. More particularly, it is desired to provide a clear antiperspirant and/or deodorant composition having good efficacy, attractive appearance and which leaves no visible (white) residue upon application and after drying.

Thus, it is an object of the present invention to provide a base composition, in which a cosmetically active material can be incorporated to form a cosmetic composition for example, an antiperspirant and/or deodorant, wherein the base composition is thickened using a gelling agent and wherein the base composition can have increased (high) levels of silicone fluid (for example, volatile and non-volatile silicone liquids). Objects of the present invention also include providing a cosmetic composition including this base composition and cosmetically active materials and methods of using this cosmetic composition.

It is a further object of the present invention to provide such base compositions which do not need particulates and/or conventional gelling agents (such as stearyl alcohol and hydrogenated castor oil) as thickening agents, and which can have increased levels of silicone fluids.

It is a further object of the present invention to provide such base compositions and cosmetic compositions made therewith, which can have increased amounts of silicone fluids, and which are also clear (transparent).

It is another object of the present invention to provide such base composition and such cosmetic composition, which can have high levels of silicone fluid, and which can be provided in thickened form as a cream (as a semi-solid or soft solid), as a gel or as a stick, depending upon the amount of the thickening agent incorporated in the composition.

It is yet another object of the present invention to provide an antiperspirant or deodorant composition, which is highly efficacious and leaves no visible (white) residue, which is thickened using a gelling agent, and which can contain increased (high) amounts of silicone fluid.

It is a further object of the present invention to provide a clear antiperspirant or deodorant cosmetic composition which has an attractive appearance and which is highly efficacious, which comprises a base composition thickened by incorporating therein a gelling agent, and which can contain large amounts of silicone fluids, and to provide a method of using such composition.

It is an overall object of the present invention to provide siloxane polymers which can be used as gelling agents to thicken cosmetic compositions, which polymers are compatible with large amounts of silicone fluids and can gel the silicone fluids (for example, volatile or non-volatile silicone liquids).

It is an object of particular embodiments of the invention to provide a vehicle for a thickened (for example, solid) cosmetic composition in which a cosmetic active ingredient can be incorporated, utilizing, for example, a polyurethane, polyurea or polyamide gelling agent, which vehicle and resulting cosmetic composition have improved application properties (including reduced tack), and a method of forming the same. It is also an object of this particular embodiment of the invention to provide a gelling agent or co-gelling agent for such vehicle and cosmetic composition.

It is a further object of particular embodiments of the present invention to provide a solid cosmetic composition (for example, a gel or stick composition), containing a cosmetically active ingredient and polyurethane, polyurea and/or polyamide gelling agents, which can be a clear composition, having reduced tack both upon and after application, and a method of forming the same.

It is a still further object of various embodiments of the present invention to provide a solid cosmetic composition, utilizing a polyurethane, polyurea and/or polyamide gelling agent, and which has increased compatibility with silicone fluids (for example, cyclomethicone or dimethicone liquids), allowing creation of compositions which contain high levels of silicone fluids (such as these silicone oils), and a method of forming the same.

It is another object of particular embodiments of the present invention to provide solid cosmetic compositions utilizing polyurethane, polyurea and polyamide gelling agents, which compositions have improved cosmetic and application properties, including having reduced tackiness and stickiness, and a method of producing the same.

It is a still further object of particular embodiments of the present invention to provide an antiperspirant and/or deodorant solid (for example, gel or stick) composition, containing deodorant and/or antiperspirant active materials, thickened using a polyurethane, polyurea or polyamide gelling agent, which cosmetic composition can be clear or at least translucent, the cosmetic composition containing increased amounts of silicone fluids (for example, cyclomethicone and/or dimethicone) and having reduced tackiness and stickiness both upon and after application, and a method of making the same.

SUMMARY OF THE INVENTION

The foregoing objects are achieved by the present invention which comprises using as gelling agents polymers which (1) contain both siloxane groups and hydrogen-bonding groups to thicken compositions containing silicone fluids (volatile and/or non-volatile silicone fluids); (2) are non-flowable solids at room temperature; and (3) dissolve in a fluid which contains silicone at a temperature of 25–250 degrees C to form a translucent or clear solution at a temperature in this range. The base composition formed from the polymers and the silicone fluids (optionally with the addition of other solvents) is then combined with at least one active ingredient (which itself may need a further vehicle to be incorporated into the base composition) and other optional ingredients such as fragrance, emollients (especially silicone-miscible emollients), coloring agents, fillers, antibacterials (antimicrobials) and other conventional ingredients known to those in the art for formulating such products to form cosmetic compositions.

The base compositions according to the present invention include (1) at least one silicone fluid and, (2) as a thickening agent, a gelling agent which is a polymer that is soluble in the silicone fluid and that can form a gel from a solution in the silicone fluid, wherein this siloxane polymer has (a) siloxane groups, and (b) hydrogen-bonding groups such that the gel can be formed. By soluble in the silicone fluid, we mean that the polymer can be dissolved in the silicone fluid at least at elevated temperatures (but below the boiling point of the silicone fluid).

By siloxane groups we mean groups having siloxane units:

(for example, 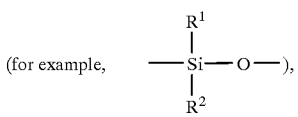), where $R^1$ and $R^2$ are each independently selected from the group consisting of methyl, ethyl, propyl, isopropyl and phenyl wherein the phenyl is optionally substituted independently by 1, 2 or 3 of methyl and ethyl) in the polymer. The siloxane units can be in the main chain, in pendant chains or in both the main chain and in pendant chains. The siloxane units occur in segments

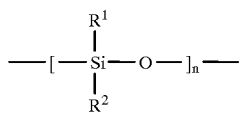

in the polymer where each segment of repeating siloxane units has a number "n" (average number of siloxane units) independently selected from the range of 1–1000, more particularly in the range of 1–300, and even more particularly in the range of 10–100.

The polymers described as thickening agents (also called gelling agents herein) also contain hydrogen-bonding groups (that is, polar groups) selected from the group consisting of ester groups, urethane groups, urea groups, thiourea groups, amide groups, and a combination of such groups in the same polymer. Examples of polymers which contain more than one of such groups are urea-urethane compounds. Mixtures of polymers containing only one type of hydrogen bonding group each are also included in the scope of the invention.

It should be noted that ester groups are capable of hydrogen-bonding only in conjunction with X—H groups (for example, X being nitrogen or oxygen) such as amide, urethane, urea and thiourea groups. Polyester polymers only by themselves may not function as gellants, but polyester copolymers containing other groups, such as urea groups, could act as thickening agents of compositions according to the present invention. Thus, hydrogen bonding is most important in substances in which a hydrogen atom is bonded to nitrogen or oxygen. The N—H and O—H bond dipoles are capable of interacting with an unshared electron pair on the nitrogen or oxygen atom of an adjacent molecule. It is this electrostatic attraction between the X—H bond dipole of one molecule and the unshared electron pair of another molecule that constitutes hydrogen bonding. It is possible to have hydrogen bonding arrangements of the kind of X—H . . . Y for cases where X and Y are, for example, N or O (the dotted line segment between "H" and "Y" refers to the hydrogen bond between the X—H dipole and the unshared electron pair of Y). The hydrogen-bonding groups can be provided at various locations of the polymer. That is, the hydrogen-bonding groups can be provided within the main chain, on side chains off the main chain, at the terminal ends of the main chain, or at locations such that the polymer is tetraterminated with hydrogen-bonding groups.

The number and location of the siloxane units and the hydrogen bonding units are selected so that the polymers are non-flowable solids at room temperature (for example from 16 degrees–30 degrees C and more particularly from 18–25 degrees C); and dissolve in a fluid which contains silicone at a temperature of 25–250 degrees C to form a translucent or clear solution at a temperature in this range.

The silicone fluids to be incorporated in compositions according to the present invention are those conventionally utilized in cosmetic compositions. These include linear siloxanes known as dimethicones, linear siloxanes containing an aromatic substitution such as phenyl trimethicone and the various cyclic siloxanes having from 4–6 members in a ring optionally substituted by C1–C6 alkyl or phenyl, particularly cyclic dimethyl siloxanes such as cyclomethicones. Mixtures of such silicone fluids may also be used. Suitable volatile silicone liquids are described in U.S. Pat. No. 5,102,656 to Kasat, referenced above. Examples of other known silicone fluids for use in cosmetic compositions are disclosed in U.S. Pat. No. 4,853,214 to Orr, referenced above and are suitable for use in this invention. Other particular examples include linear volatile silicone fluids, for example, silicone liquids conventionally used in cosmetic compositions.

The cosmetic compositions according to the present invention include the at least one silicone fluid and the siloxane-containing polymer as well as at least one cosmetically active material, incorporated in the composition in an amount sufficient to have a functional effect. Such actives include, but are not limited to fragrances, sunscreens, antiperspirants, deodorants and antibacterials. For example, where the composition is a composition to protect skin from the sun, a sufficient amount of a sun-screening agent is provided in the composition such that when the composition is applied to the skin, the skin is protected from the harmful effects of the sun (for example, is protected from ultraviolet rays from the sun).

Clear (transparent) base compositions, and clear (transparent) cosmetic compositions, that are thickened (more viscous) as compared to the viscosity of the silicone fluids, can be achieved using these siloxane-containing polymers as thickening agents.

The compositions of the present invention can also be utilized to form clear antiperspirant compositions having multiphase systems, such multiphase systems having a polar (for example, water) phase (including an antiperspirant active material) and an oil phase (including the silicone fluids and siloxane polymer). In order to provide a clear multiphase system, refractive indices of the oil and polar phases desirably should be matched, as done conventionally in the art.

As noted above, the polymers used as thickening agents in base and cosmetic compositions of the present invention contain both siloxane units and hydrogen-bonding groups. The siloxane units provide compatibility with the silicone fluid (for example, with the cyclomethicones), while the hydrogen-bonding groups facilitate gelation by achieving hydrogen bonding, for example, upon cooling a solution of the siloxane polymer in the silicone fluid.

The polymers containing siloxane units and hydrogen bonding groups incorporated as thickening agents in base and cosmetic compositions according to the present invention can be copolymers in which: (1) a siloxane diamine (that is, a molecule that contains at least one siloxane unit and which contains two amino groups) is reacted with a diacid (or diacid derivative), diisocyanate and/or a diisothiocyanate, to produce amide groups, urea groups or thiourea groups, respectively, as the hydrogen-bonding groups; (2) a siloxane diacid (or siloxane diacid derivative) is reacted with a diol or diamine, to produce ester groups or amide groups, respectively; or (3) a siloxane diol is reacted with a diisocyanate, to produce urethane groups as the hydrogen-bonding groups. As noted above, the polymers used in this invention can also be formed to contain a combination of the hydrogen-bonding groups, by appropriately reacting the relevant monomers such as, for example, a siloxane diamine, diacid or diol with a combination of diisocyanates and diacids, diisocyanates and diols.

According to one aspect of the invention which provides polyurethane compounds, a siloxane diol may be reacted with a diisocyanate to form the polyurethane. Suitable diols include those where n=1–100 repeating units, optionally substituted on at least one of the silicones by copolymer units having at least one of methyl, ethyl, propyl, isopropyl or aryl (for example, phenyl) groups. Suitable diisocyanates include: (a) C1–C15 linear and branched aliphatic groups optionally substituted by at least one member of the group consisting of C1–C15 alkyl and C5–C10 aryl; (b) C5–C10 cyclic aliphatic and aromatic groups optionally substituted by at least one member of the group consisting of C1–C15 alkyl and C5–C10 aryl. Examples of particular diisocyanates include hexamethylene diisocyanate, toluene diisocyanate and isophorone diisocyanate. Comb-branched variations containing hydroxyl groups may also be used as reagents and reacted with monoisocyanate such as phenyl isocyanate.

According to another aspect of the invention which provides polyurea compounds, a siloxane diamine may be reacted with a diisocyanate (for example, hexamethylene diisocyanate, toluene diisocyanate or isophorone diisocyanate) to form the polyurethane. Comb-branched variations containing amine groups may also be used as reagents and reacted with monoisocyanate such as phenyl isocyanate.

According to yet another aspect of the present invention which provides polyamide compounds, the polymer is a copolymer formed from monomers or oligomers including a siloxane oligomer such as a copolymer formed by reacting an oligosiloxane diamine with a dimer acid. Polyamide gelling agents useful in this invention can also be formed by: (1) silyl amidation or silyl esterification of dimer-based polyamides (for example, reacting free acid end-sites on an original polyamide with oligosiloxanes each containing at least one amine group, or with oligosiloxane alcohols or diols); (2) substituting an oligosiloxane diamine for the diamine in an original polyamide (transamidation at elevated temperatures, such as at least 150 degrees C and more particularly, at least 200 degrees C); (3) grafting pendant oligosiloxane groups on an original polyamide; or formed by conventional techniques, some of which are discussed below.

The compounds of the present invention exhibit desirable properties from the standpoint of their compatibility with siloxane units compounds such as cyclomethicone. This is in distinction to our recently issued U.S. Pat. No. 5,500,209 reciting the use of polyamides as gelling agents. For example, in the case of an amide thickening agent of the invention, such an amide thickening agent enhances compatibility of a silicone fluid, such as cyclomethicone and/or dimethicone, in the composition, so that increased amounts of the silicone fluid can be included in the composition without adversely affecting other properties (for example, clarity) of the composition. For example, the composition can include more than 50% by weight of a silicone oil. Moreover, by incorporating increased amounts of the silicone fluid in the composition, tackiness and stickiness of the composition can be reduced. In addition, various of the amide thickening agents (as well as the other agents described herein such as polyurethane and polyurea agents) having silicon-containing moieties per se, described below, provide a gel which is less tacky or sticky than, for example, various of the polyamide thickening agents described in the aforementioned U.S. Pat. No. 5,500,209, even without the increased amounts of silicone oil.

Cosmetic compositions according to the present invention can also include surface active agents and/or solvents for the cosmetically active material. For example, where the composition is an antiperspirant composition, containing antiperspirant active material, the antiperspirant active material can be included in the composition in a solution in, for example, water, ethanol and/or propylene glycol, which is not miscible with the silicone fluid, and the composition can also include surface active agents so as to disperse the solution of antiperspirant active material in the composition. Where the composition according to the present invention is a deodorant composition, the composition can include conventional fragrances and/or antibacterial (antimicrobial) agents as deodorant active materials.

Base and cosmetic compositions according to the present invention can easily be manufactured by methods known to those skilled in the art such as by using known mixing procedures. For example, the silicone fluids and siloxane-containing polymers can be mixed at elevated temperatures so as to dissolve the polymer in the silicone fluids, with cosmetically active ingredients being added to the mixture of silicone fluids and polymer. Upon cooling the mixture, the polymer forms a gel from the solution, achieving the desired product. The base compositions of the present invention are thermally reversible gels; that is, they form gels upon being cooled and are liquefied when heated.

Where the product is a stick product, the molten product, at elevated temperatures, can be poured into dispensing containers and allowed to cool and harden therein. Where the product is a soft solid or cream, the product can be packaged into conventional dispensing containers having a top surface with slots therein, as conventionally done in the art.

The compositions according to the present invention can be used as sticks, gels and creams as conventionally used by the consumer. For example, where the compositions of the present invention are a deodorant or antiperspirant composition containing deodorant and/or antiperspirant active materials, the compositions can be rubbed against the skin (for example, in axillary regions of the human body), so as to deposit the active material on the skin in order to reduce body malodor and/or reduce flow of perspiration from, for example, axillary regions.

When a cosmetic composition according to the present invention is in the form of a stick product, the composition can be applied by elevating the stick out of the package so as to expose the end of the stick, and then rubbing the end of the stick on the skin in order to deposit stick material (including the cosmetically active material) on the skin. When the composition according to the present invention is in the form of a gel composition, packaged in a dispensing container having a top surface with slots or pores, the gel is extruded from the dispensing container through the slots or pores and applied to the skin by rubbing the gel material that has been extruded through the top surface of the container on the skin.

Accordingly, by the present invention a cosmetic composition can be formed using, as a thickening agent, a polymer gelling agent containing siloxane units and hydrogen-bonding groups, so as to have increased compatibility with silicone fluid (such that increased amounts of silicone fluid can be utilized in the composition), yet which can gel from a solution in the silicone fluid. Utilizing this polymer as a thickening agent in the compositions containing silicone fluids, creams, gels and sticks, and soft (and mushy) or firm (and hard) compositions can be formed, depending on the concentration of the thickening agent (including the polymer containing siloxane units and hydrogen-bonding groups) incorporated in the composition. Moreover, various cosmetic compositions can be formed, depending on the cosmetically active materials incorporated, and clear (for example, transparent) cosmetic compositions can be formed. In particular, through use of the present invention, deodorant and/or antiperspirant compositions, in the form of creams (including soft solids and semi-solids), gels and sticks, which have high efficacy, have an attractive appearance (for example, which can be clear or at least translucent), and leave substantially no visible (white) residue either upon application or upon drying, can be achieved.

The siloxane units can, illustratively, be provided as part of the main chain of the polymer (for example, the polymer being a siloxane polymer). The hydrogen-bonding groups can be provided as part of the main chain, for example, of a polymer which contains siloxane units in the main chain, at ends of the main chain (terminating the ends of the main chain), or on side chains off the main chain. Various structures of the siloxane polymer are schematically illustrated in FIGS. 1–5. In these figures, the repeat units x, y and n are variable and can have values(which are actually average values) in the range of:

$x=1-500$, more particularly 1–100, and most particularly 1–50;

$y=0-500$, more particularly 0–100, and most particularly 0–50;

$n=1-500$, more particularly 1–300, and most particularly 1–100.

Figure 1:
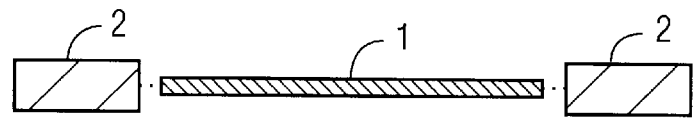
FIGS. 1–5 schematically show polymer gelling agents, which can be incorporated as a thickening agent in compositions of the present invention, having siloxane units in the main chain, and hydrogen-bonding groups respectively in five different locations of the polymer.
Figure 2:
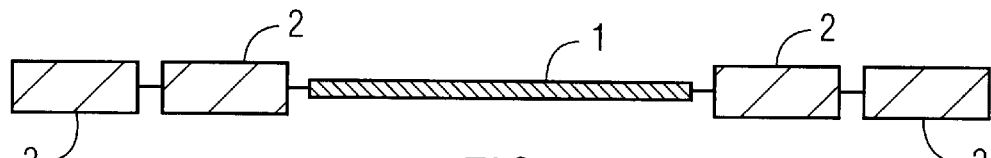
Figure 3:
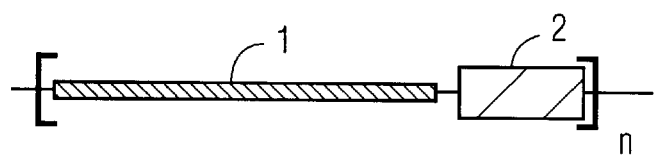
Figure 4:
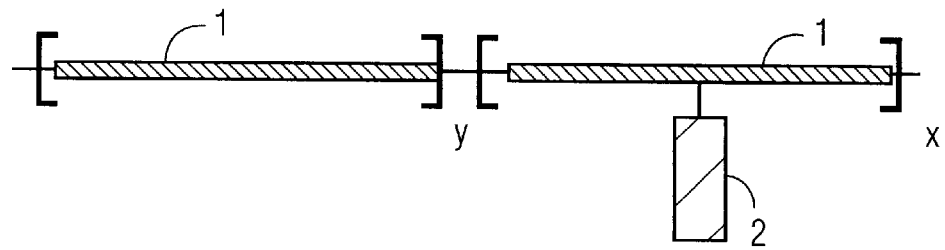
Figure 5:
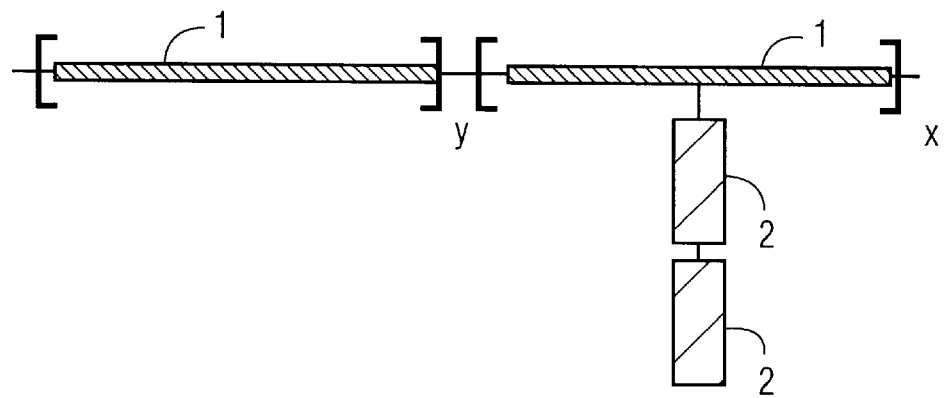

In these figures, reference character 1 represents the siloxane-containing main chain, and reference character 2 represents the hydrogen-bonding group. In FIG. 1, the hydrogen-bonding group is provided at the ends of the main chain. In FIG. 2, the main chain 1 is tetraterminated by hydrogen-bonding groups 2 (four hydrogen-bonding groups are provided at the ends of the main chain; that is, there are two hydrogen-bonding groups at each chain end, giving four hydrogen-bonding groups per molecule). In FIG. 2A, the main chain is tetraterminated by four separate groups, two at each end. In FIG. 3, the hydrogen-bonding groups 2 are provided within the main chain 1, as part of the repeating unit. In FIGS. 4 and 5, the hydrogen-bonding groups 2 are provided on side chains to the main chain 1, pendant to the main chain; FIGS. 4 and 5 respectively show structures with one and with two hydrogen-bonding groups on each branch. In the Figures, n, x and y are variable numbers, however n and x each cannot have a value of zero. Particular values for each of n, x and y are selected so that the limitations described for the polymers used as gelling agents are met.

DETAILED DESCRIPTION OF THE INVENTION

The invention is described herein as comprising a base composition comprised of at least one silicone fluid and at least one gelling agent (also called thickening agent) selected from a group of compounds containing both siloxane groups and hydrogen bonding groups. If the combined amounts of the silicone fluid and the gelling agent do not equal 100 percent on a weight basis then an additional solvent is also added. Cosmetic compositions may then be made by combining the base composition with one or more additional solvents, active ingredients, one or more vehicles to allow the active ingredient to combine more easily (or with more desirable properties) with the base composition, and other ingredients used by those in the art to formulate cosmetically acceptable products including fragrances, coloring agents, fillers, emollients and antibacterials.

In the base composition, the gelling agent can be used in an amount of 1–60 percent by weight, more particularly 5–30 percent by weight and most particularly 10–20 percent by weight. It is preferred that the gellant not exceed 50 percent by weight of the base composition. The silicone fluid portion is in the range of 0.5–95 percent by weight, more particularly 10–80 percent by weight, even more particularly 20–75 percent by weight and most particularly 30–70 percent by weight. Optionally, additional solvent or mixtures of solvents may be added to form the base composition. Suitable additional solvents are those which are either themselves or in mixtures with other solvents miscible in the originally selected silicone fluid (for example, C14–C20 fatty alcohols, isopropyl myristate, adipate palmitate and isostearate). By using the base and cosmetic compositions of the present invention the upper range of the amounts of silicone fluids which can be incorporated in the gel is higher than amounts which can be incorporated in conventional compositions.

Optionally the gelling agent can also be endcapped. The endcapping may be effected with the use of an agent selected from the group consisting of C1–C20 aliphatic monohydric alcohols, C1–C6 aliphatic amines, phenyl amine optionally substituted by 1–3 members selected from C1–C6 aliphatics, C1–C20 aliphatic acids and C1–C20 aliphatic acid chlorides.

The base composition is then mixed with the other ingredients listed elsewhere so that the final cosmetic composition can be made. Such additional ingredients can be used in amounts of 0.5–85 percent, more particularly 1–75 percent and even more particularly 2–55 percent where the percentages are based by weight on the base composition as 100 percent. The lower percent ranges include formulations where only fragrances are used and the upper ranges include formulations containing active antiperspirant ingredients. An antiperspirant active itself (excluding any vehicle for adding the active to the formulation) can be present in the final cosmetic formulation in an amount of from 5–25 percent.

While siloxane units have been defined above, more particular values for $R^1$ and $R^2$ are methyl, ethyl and phenyl and an even more particular value for each of $R^1$ and $R^2$ is methyl.

While various hydrogen bonding groups have been described above, more particular values for such groups include urea, urethane and amide; and an even more particular group is urea. A particularly preferred polymer is one which contains more than one urea functionality, such as those made with siloxane diamines where n=10–300. A particular polymer is made with a siloxane diamine where n=30 and hexamethylenediisocyanate such as described in Synthetic Example 1 and formulated in Formulation Example 1.

While various silicone fluids have been described above, particular silicone fluids useful in the invention include cyclomethicone, dimethicone and phenyldimethicone.

Throughout the present disclosure, the present invention is described primarily in connection with gel or stick antiperspirant and/or deodorant compositions, including clear gel or stick antiperspirant or deodorant compositions. However, the present invention is not limited to gel or stick compositions, or to antiperspirant or deodorant compositions. For example, the composition according to the present invention can be a sunscreen composition. Thus, depending on the cosmetically active ingredients included in the composition, the composition can be any of various cosmetic compositions. Various cosmetically active materials incorporated in cosmetic compositions are disclosed in U.S. Pat. No. 4,322,400 to Yuhas, the contents of which are incorporated herein by reference in their entirety.

Throughout the present specification, "antiperspirant active" and "deodorant active" materials are discussed. Both types of materials contribute to reduction of body malodor, for example, axillary malodor. By reduction of body malodor, it is meant that, generally, there is less body malodor after application of the composition to a person's skin, as compared to a person's malodor without application of the composition. Such reduction can be due to a masking of the malodor, absorption and/or chemical reaction of the malodorous material, reduction of the levels of the bacteria producing the malodorous materials, for example, from perspiration, reduction of perspiration, etc. The antiperspirant active materials, when utilized in appropriate amounts, primarily act to reduce malodor by reducing perspiration; the antiperspirant active materials can also have a deodorant function, for example, as an antimicrobial or bacteriostatic agent. The deodorant active materials do not substantially reduce perspiration, but reduce malodor in other ways, for example, as fragrances masking the malodor or reducing the malodor intensity, as absorbents, as antimicrobial (bacteriostatic) agents, as agents chemically reacting with malodorous material.

Throughout the present specification, where compositions are described as including or comprising specific components or materials, or where methods are described as including or comprising specific steps, it is contemplated by the inventors that the compositions of the present invention also consist essentially of, or consist of, the recited components or materials, and also consist essentially of, or consist of, the recited steps. Accordingly, throughout the present disclosure any described composition of the present invention can consist essentially of, or consist of, the recited components or materials, and any described method of the present invention can consist essentially of, or consist of, the recited steps.

A desired feature of the present invention is that a clear, or transparent, cosmetic composition, (for example, a clear or transparent deodorant or antiperspirant composition) can be provided. The term clear or transparent (that is, clarity) according to the present invention is intended to connote its usual dictionary definition; thus, a clear, for example, stick or gel antiperspirant composition of the present invention allows ready viewing of objects behind it. By contrast, a translucent composition, although allowing light to pass through, causes the light to be scattered so that it will be impossible to see clearly objects behind the translucent composition. An opaque composition does not allow light to pass therethrough. Within the context of the present invention, a gel or stick is deemed to be transparent or clear if the maximum transmittance of light of any wavelength in the range 400–800 nm through a sample 1 cm thick is at least 35%, preferably at least 50%. The gel or stick is deemed translucent if the maximum transmittance of such light through the sample is between 2% and less than 35%. A gel or stick is deemed opaque if the maximum transmittance of light is less than 2%. The transmittance can be measured by placing a sample of the aforementioned thickness into a light beam of a spectrophotometer whose working range includes the visible spectrum, such as a Bausch & Lomb Spectronic 88 Spectrophotometer. As to this definition of clear, see European Patent Application Publication No. 291,334A2. Thus, according to the present invention, there are differences between transparent (clear), translucent and opaque compositions.

In a particular embodiment of the invention a polyurethane, polyurea, polyurea-urethane or polyamide is used to form a solid composition of the present invention which is a clear, or at least a translucent, gel or stick (for example, antiperspirant gel or stick composition).

This polymer gelling agent, for example, can be a siloxane polymer (siloxane units on the main chain) containing the hydrogen-bonding groups. The thickening agent can consist of this polymer (or a mixture of these polymers), or can contain this polymer admixed with other thickening agents (including conventional gelling agents). The siloxane units provide compatibility with the silicone fluids. The hydrogen-bonding groups (which are polar groups) are utilized for cross-linking purposes so as to form the gel.

The present invention also contemplates incorporating a cosmetically active ingredient (such as a fragrance, an antiperspirant active material, a sunscreen agent, etc.) in the base composition, so as to form the cosmetic composition. In one particular embodiment of the invention, the base composition is a gel of the polymer formed from a solution of the gelling agent (containing siloxane units and hydrogen-bonding groups) and the silicone fluid and is clear. In addition, cosmetic compositions according to the present invention, having an active agent incorporated in the base composition, can also be formulated to be clear such as by matching the refractive indices of the additional components to the base composition.

The thickening agent should be included in the cosmetic composition in an amount sufficient to form a composition of a desired firmness (for example, a cream or soft-solid, gel, or stick).

The base and cosmetic composition according to the present invention may be soft (and mushy) or firm (and hard), depending on the amount of the thickening agent included in the composition. Thus, depending on the amount of thickening agent (for example, polymer containing siloxane units and hydrogen-bonding groups) incorporated in the composition, the composition can be in the form of a cream (for example, semi-solid or soft solid) or gel, and can even be formulated as a stick.

Compositions according to the present invention are thermoreversible gels; that is, the gels are formed by cooling a solution of the polymer in the silicone fluids, but the gel can be broken (formed back into a liquid) by heating the gel.

The gels of the present invention include silicone fluids (for example, silicone liquids). These fluids can be volatile or non-volatile and include, illustratively (and not of a limiting nature), phenyl trimethicone, cyclomethicones and/or dimethicones.

Preferably, the silicone fluid includes cyclomethicones. The cyclomethicone used (that is, ring size of the cyclomethicone) has an effect on the hardness of the gels formed. That is, cyclomethicone of a five-member ring (that is, D5 used in Dow Corning 245 fluid) produces a softer gel than that produced utilizing D6 cyclomethicone (Dow Corning 246 fluid). As the ring size of the cyclomethicone increases, the rigidity of the gel system formed increases. As described above, particular examples of suitable cyclomethicones include those having rings of 4–6 members.

Where the composition contains an antiperspirant active, any of the known antiperspirant active materials can be utilized. These include, by way of example (and not of a limiting nature), aluminum chlorohydrate, aluminum chloride, aluminum sesquichlorohydrate, zirconyl hydroxychloride, aluminum-zirconium glycine complex (for example, aluminum zirconium trichlorohydrex gly, aluminum zirconium pentachlorohydrex gly, aluminum zirconium tetrachlorohydrex gly and aluminum zirconium octochlorohydrex gly), aluminum chlorohydrex PG, aluminum chlorohydrex PEG, aluminum dichlorohydrex PG, and aluminum dichlorohydrex PEG. The aluminum-containing materials can be commonly referred to as antiperspirant active aluminum salts. Generally, the foregoing metal antiperspirant active materials are antiperspirant active metal salts. In the embodiments which are antiperspirant compositions according to the present invention, such compositions need not include aluminum-containing metal salts, and can include other antiperspirant active materials, including other antiperspirant active metal salts. Generally, Category I active antiperspirant ingredients listed in the Food and Drug Administration's Monograph on antiperspirant drugs for over-the-counter human use can be used. In addition, any new drug, not listed in the Monograph, such as aluminum nitratohydrate and its combination with zirconyl hydroxychlorides and nitrides, or aluminum-stannous chlorohydrates, can be incorporated as an antiperspirant active ingredient in antiperspirant compositions according to the present invention.

Antiperspirant actives can be incorporated into compositions according to the present invention in amounts in the range of 0.1–30%, preferably 15–25%, by weight, of the total weight of the composition. The amount used will depend on the formulation of the composition. For example, at amounts in the lower end of the broader range (for example, 0.1–10%), the antiperspirant active material will not substantially reduce the flow of perspiration, but will reduce malodor, for example, by acting as an antimicrobial material.

Where deodorant active materials are incorporated in compositions according to the present invention, so as to provide deodorant compositions, conventional deodorant fragrances and/or antimicrobial agents can be incorporated as the deodorant active materials. A fragrance would, illustratively, be incorporated in an amount of 0.5%–3.0% by weight, of the total weight of the composition; the antimicrobial/bacteriostat material, such as Triclosan, can illustratively be included in an amount of from 0.1% to about 0.5% by weight, of the total weight of the composition.

Compositions according to the present invention can include other ingredients conventionally incorporated in cosmetic compositions, including (but not limited to) perfumes, cosmetic powders, colorants, emulsifiers, etc. As for various other ingredients which can be incorporated, attention is directed to the optional components such as colorants, perfumes and fillers described in the following U.S. Patents: U.S. Pat. No. 5,019,375 to Tanner, et al (the contents of which are incorporated herein by reference in their entirety); U.S. Pat. No. 4,937,069 to Shin (the contents of which are incorporated herein by reference in their entirety); and U.S. Pat. No. 5,102,656 to Kasat (the contents of which have been previously been incorporated herein by reference in their entirety).

Inert fillers, such as corn starch, alumina and calcium carbonate, can also be incorporated in compositions according to the present invention. However, with these inert fillers as well as with other optional components, where a transparent or clear composition is desired, the optional components should not unduly disadvantageously affect the clarity.

Where the composition is an antiperspirant composition, the composition can also include a solvent for the antiperspirant active. This solvent, which is not miscible with the silicone fluid, can illustratively be water, ethanol, propylene glycol and/or dipropylene glycol. Where the antiperspirant active is utilized in a solution in the solvent, it may be necessary to match refractive indices of the antiperspirant active solution with that of the oil portion of the composition, in order to achieve a transparent or clear composition. Where the antiperspirant active material is suspended in the base composition as particulate material, it may also be necessary to match refractive indices of the active material and base composition to obtain a clear or transparent composition. Such refractive index matching is a technique known in the art, and is shown in PCT (International Application) Publication No. WO/05767, the contents of which have previously been incorporated herein by reference in their entirety. The solvent for the antiperspirant active material can be included in the composition in an amount within the range of 0–75%, preferably 0–25%, by weight, of the total weight of the composition.

The solvent for the thickening agent is included in the composition in an amount sufficient such that the thickening agent can be dissolved therein and gelled therefrom, and includes a silicone fluid (for example, a silicone oil, such as cyclomethicone and/or dimethicone). Thus, the thickening agent can be dissolved in the solvent and gelled therefrom, for example, upon cooling the composition during manufacture thereof.

The solvent is not limited to only those materials containing a silicone fluid, and can contain other solvents for the thickening agent as long as such other solvents are compatible with, for example, the active cosmetic material and do not disadvantageously affect, for example, clarity of the composition, especially where it is desired to provide a clear cosmetic composition. For example, as defined in the CTFA International Cosmetic Ingredient Dictionary (4th Ed. 1991), an additional solvent included in the composition can be C12–15 alkyl lactate (which is an ester of lactic acid and C12–15 alcohols); one such C12–15 alkyl lactate is vended by Van Dyk & Co., Inc. as "Ceraphyl 41". Solvents for the polyamide gelling agent disclosed in U.S. Pat. No. 5,500,209 can be used in compositions of the present invention. Illustratively, and not to be limiting, the solvents can include esters (for example, the C12–15 lactate ester described above as Ceraphyl 41), silicone fluids (for example, cyclomethicone, dimethicone), guerbet alcohols having 8–30 carbons, particularly 12–22 carbons (for example, isolauryl alcohol, isocetyl alcohol, isostearyl alcohol), fatty alcohols (for example, stearyl alcohol, myristyl alcohol, oleyl alcohol), ethanol, and ethoxylated alcohols (for example, the polyethylene glycol ether of lauryl alcohol that conforms to the formula $CH_3(CH_2)_{10}CH_2(OCH_2CH_2)_NOH$ where n has an average value of 4 (also called laureth –4)). Other illustrative solvents include:

(a) PPG-14 butyl ether, where the "PPG-14" portion is the polymer of propylene oxide that conforms generally to the formula $H(OCH_2C(CH_3)H)_NOH$, where n has an average value of 14;

(b) isopropyl myristate;

(c) PPG-2 myristyl ether propionate which is the ester of propionic acid and the polypropylene glycol ether of myristyl alcohol that conforms to the formula $CH_3(CH_2)_{12}CH_2(OCH(CH_3)CH_2)_2O\text{—}C(O)CH_2CH_3$; and (d) PPG-13 myristyl ether which is the polypropylene glycol ether of myristyl alcohol that conforms to the formula $CH_3(CH_2)_{12}CH_2(OCH(CH_3)CH_2)_nOH$ where n has an average value of 13. Mixtures of solvents can also be used. Of course, the gelling agent must be soluble in the solvent system, at least at elevated temperatures, as described in U.S. Pat. No. 5,500,209.

Compositions according to the present invention desirably include silicone-miscible emollients. Illustrative emollients, which are not limiting of the present invention, would include guerbet alcohols (such as isocetyl alcohol or isostearyl alcohol); esters (such as isopropyl palmitate, isopropyl isostearate, octyl stearate, hexyl laurate and isostearyl lactate); a liquid mixture of hydrocarbons which are liquids at ambient temperatures (such as petroleum distillates and light mineral oils); and ethanol. The silicone-miscible solvents (also called emollients) can be included in the compositions of the present invention in amounts within the range of 0–70%, preferably 0–25%, by weight, of the total weight of the composition.

Where a multi-phase system is utilized as the composition of the present invention, preferably the composition includes a surfactant or surfactant blend. Surfactants illustratively include alkanolamides (such as N-alkyl pyrrolidone), ethoxylated amides (for example, the polyethylene glycol amide of tallow acid that conforms generally to the formula $RC(O)\text{—}NH\text{—}(CH_2CH_2O)_nH$ where RCO— represents the fatty acids derived from tallow and n has an average value of 50 (also called PEG-50 tallow amide)); amine oxides (for example, cocamidopropylamine oxide); ethoxylated carboxylic acids (for example, the polyethylene glycol diester of lauric acid that conforms generally to the formula $CH_3(CH_2)_{10}C(O)\text{—}(OCH_2CH_2)_nO\text{—}C(O)(CH_2)_{10}CH_3$ where n has an average value of 8 (also called PEG-8 dilaurate)); ethoxylated glycerides (for example, a polyethylene glycol derivative of Castor Oil with an average of 4 moles of ethylene oxide (also called PEG-4 castor oil)); glycol esters (for example, propylene glycol ricinoleate); monoglycerides (for example, glycerol myristate); polyglyceryl esters (for example, polyglyceryl-4 oleyl ether); polyhydric alcohol esters and ethers (for example, sucrose distearate); sorbitan/sorbitan esters (for example, sorbitan sesquiisostearate); triesters of phosphoric acid (for example, trioleth-8 phosphate (a material which is predominantly the triester of phosphoric acid and ethoxylated oleyl alcohol with an average of 8 moles of ethylene oxide)); ethoxylated alcohols (for example, laureth-4); ethoxylated lanolin (for example, a polyethylene glycol derivative of Lanolin with an average of 20 moles of ethylene oxide (also called PEG-20 lanolin)); ethoxylated polysiloxanes (for example, dimethicone copolyol); propyloxated polyoxyethylene ethers (for example, the polyoxypropylene, polyoxyethylene ether of cetyl alcohol that conforms generally to the formula $CH_3(CH_2)_{14}CH_2(OCH(CH_3)CH_2)_x(OCH_2CH_2)_yOH$ where x has an average value of 5 and y has an average value of 20 (also called PPG-5 ceteth-20)); and alkylpolyglycosides (for example, lauryl glucose). The surfactant (or surfactant blend) includes non-ionic compounds, and can also include blends thereof with cationic (for example, the polyethylene glycol amine of tallow acid that conforms generally to the formula $R\text{—}NH\text{—}(CH_2CH_2O)_nH$ (also called PEG-15 tallow amine)) or anionic (for example, sodium lauroyl laurate which is the sodium salt of the lauric acid ester of lauric acid) surfactants.

The surfactant or blend thereof incorporated in compositions according to the present invention can, illustratively, be included in amounts of 0–15%, preferably 0–4%, by weight, of the total weight of the composition.

As indicated previously, the compositions according to the present invention can be creams (semi-solids or soft-solids), gels or sticks, depending on amounts of thickening agent incorporated in the composition. It is difficult to quantitatively distinguish between a cosmetic "gel" and a cosmetic "stick". Generally, a gel is more viscous than a liquid or than a paste which fails to retain its shape; however, it is not as rigid as a stick. Typically, it is understood that gels are soft, deformable products while sticks are free-standing solids. In the cosmetic field, systems are classified as gels or sticks depending on their viscosity or hardness alone; typically, it is understood that gels are soft, deformable products while sticks are strictly free-standing solids. For example, by Theological analysis, a commercial deodorant stick has been determined to have a plateau storage modulus $G'(\omega)$ of roughly $10^5$ Pa and a complex viscosity of $10^6$ Pa second (both at an angular frequency of 0.1 rad-sec). On the other hand, a commercial antiperspirant gel has been determined to have a $G'(\omega)$ value of roughly $10^3$ Pa and a complex viscosity of $10^4$ Pa second (at 0.1 rad-sec).

Cosmetic compositions according to the present invention include both a thickening agent and a solvent for the thickening agent (in the present application, the thickening agent and solvent for the thickening agent provide a vehicle for the active cosmetic material, and have been so designated as a vehicle).

The polymer gelling agents utilized according to the present invention can be defined in terms of techniques utilized for forming these polymers. For example, for one particular group the polymer gelling agent may include siloxane copolymers in which a siloxane diamine is reacted with a diacid and/or diacid derivative (generically called diacids), diisocyanate or a diisothiocyanate to produce a copolymer with amide groups, a copolymer with urea groups, and a copolymer with thiourea groups, respectively. A second group of polymer gelling agents that can be incorporated in compositions according to the present invention include siloxane polymers in which a siloxane diacid and/or diacid derivative is reacted with a diol or diamine, to produce copolymers with ester or amide groups, respectively. Copolymers with ester groups would need to be used with other copolymers having, for example, urea or amide groups, or the copolymers with ester groups would also need to have, for example, urea or amide groups, in order to achieve hydrogen bonding, as discussed previously. A third group of illustrative copolymers is those in which a siloxane diol is reacted with a diisocyanate, to produce a polyurethane.

The polymer can have the hydrogen-bonding groups terminating the ends of the main chains. For example, bifunctional and tetrafunctional terminated siloxane polymers can be reacted so as to form biterminated and tetra-terminated siloxane polymers, terminated with hydrogen-bonding groups.

A polymer of this invention containing siloxane units and hydrogen-bonding groups can also be a siloxane polymer formed by reacting comb-branch siloxane polymers having pendant amino groups (for example, amino groups on a side chain), with an acid, isocyanate and/or isothiocyanate, to form polymers with amide, urea and/or thiourea groups. Thus, these comb-branch siloxane polymers are reacted with mono-functional compounds, for example, mono-isocyanates, to form the polymers containing siloxane units and hydrogen-bonding groups acting as thickening agents in the compositions of the present invention. The comb-branch siloxane polymers may have a single amino group per branch (for example, aminopropyl branches) or, alternatively, may have diamino branches (for example, aminoethylaminopropyl or aminoethyl-aminoisobutyl branches), or could contain a mixture of amino and diamino branches. An illustrative siloxane polymer with diamino branches is an amino-functional silicone polymer such as Dow Corning Q2-8220 fluid (trimethylsilylamodimethicone) which is a silicone polymer conforming generally to the formula

where x and y are proprietary to Dow Corning. As with all of the siloxane polymers which can be incorporated in compositions according to the present invention, the length of the main chain (that is, number of siloxane units) can be varied to optimize properties of the gellant; moreover, using comb-branch siloxane polymers, density of the branches could be varied to optimize properties of the gellant. The following structures (A) and (B) show illustrative comb-branch siloxanes, respectively having amino and diamino branches:

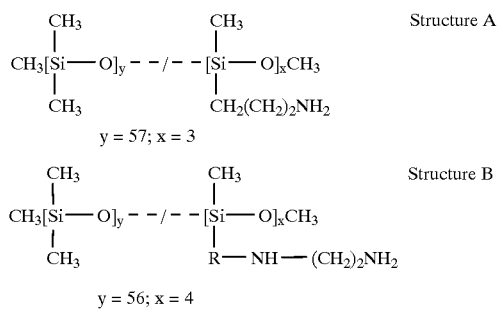

where the "/" mark indicates that the segments can be of varying lengths and in random order and where R=a straight chain aliphatic group, preferably having 1–6 carbons and more preferably having 1–3 carbons.

Illustratively, the polymer containing siloxane units and hydrogen-bonding groups can be formed by reacting a siloxane polymer, having at least three amino groups per polymer molecule, with a compound having a single monofunctional group, respective monofunctional groups (for example, an acid, isocyanate or isothiocyanate) reacting with one of the amino groups to form the hydrogen-bonding groups. The amino groups can be on side chains extending from the main chain of the siloxane polymer, whereby the hydrogen-bonding groups are formed on these side chains; or the amino groups can be at ends of the main chain, whereby the hydrogen-bonding groups are terminating groups of the polymer (for example, where four amino groups are provided on the polymer reactant, two on each end, the polymer product having hydrogen-bonding groups is a tetraterminated polymer).

As a specific procedure for forming a polymer containing siloxane units and hydrogen-bonding groups and then forming the composition of the present invention, the polymer can be produced by reaction of, for example, a siloxane diamine and a diisocyanate in a silicone solvent, so as to directly provide the gel. That is, reaction of the components to form polymers or copolymers containing siloxane units and hydrogen-bonding groups can be performed in the silicone fluid, the resulting product being dissolved in the silicone fluid, at elevated temperatures, with the temperature of the system then being decreased to form the gel.

Preferred polymers for incorporation in compositions according to the present invention are siloxane/urea copolymers which are linear and which contain urea groups as hydrogen-bonding groups in the backbone of the polymer.

An illustrative polysiloxane terminated with four urea groups (tetraterminated polysiloxane) is represented by the following Formula (I), which is the reaction product of a siloxane polymer with phenyl isocyanate as shown in the following Reaction Scheme I:

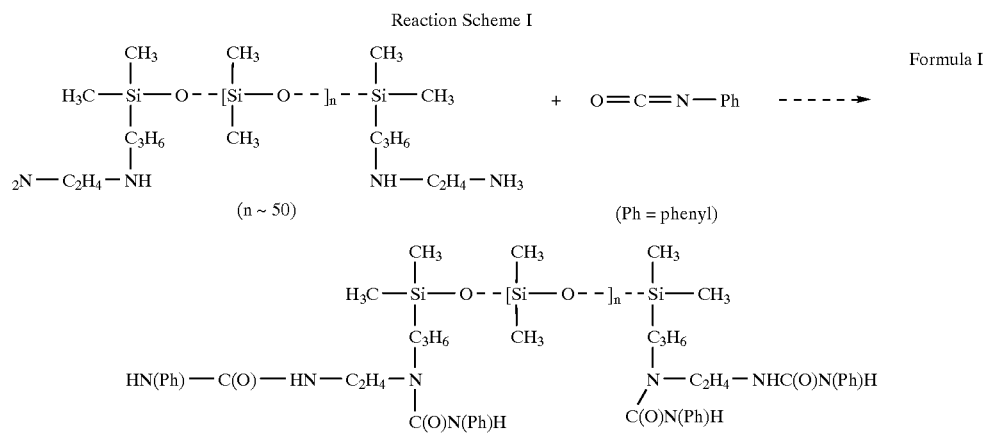

where Ph=phenyl, and n is an average and is a number from 0–300, particularly 0–100 and, for example, 50.

The tetraterminated polymer is optically clear, and soluble in chloroform, tetrahydrofuran and acetone. It swells silicone fluids such as cyclomethicone (Dow Corning 345 fluid) and dimethicone (Dow Corning 200 fluid). The cyclomethicone can be gelled at room temperature with the polymer of Formula I, when the weight percent of the polymer is roughly 50% of the total weight of the composition. The final gel has a melting point of about 25° C. and is isotropic, transparent and colorless.

It should be noted that endcapping of polymers of Formula I may also be accomplished with the use of an agent selected from the group consisting of C1–C20 aliphatic monohydric alcohols, C1–C6 aliphatic amines, phenyl amine optionally substituted by 1–3 members selected from C1–C6 aliphatics, C1C20 aliphatic acids and C1–C20 aliphatic acid chlorides.

Another illustration of such copolymerization utilizes an oligosiloxane which is terminated at both ends with α-aminopropyl groups. Such an oligosiloxane is called a siloxane diamine, a diamino siloxane oligomer, or α, ω-bis (aminopropyl) oligodimethylsiloxane. Such oligomers would have the following structure designated as Formula III:

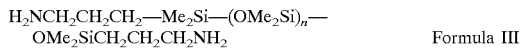

where n has an average value from 1–300 with more particular values being 10–100, even more particular values being from 10–40 and a particular group being 10–30 and Me=methyl. One example of a monomer of Formula III is available in various average lengths including 9–300 from United Chemical Technologies (Bristol, Pa.), Wacker Silicones (Adrian, Mich.), Shin Etsu (Tokyo, Japan) and Gelest (Tullytown, Pa.).

The copolymer made from diamines and either diacids or diisocyanates can include the siloxane diamine as the sole diamine material in forming the copolymer, or preferably the copolymer can also include additional diamine (such as ethylene diamine and/or hexamethylene diamine). Including such additional diamine would aid in producing a solid polymer, which can be useful in gelling fluids. Desirably, the siloxane diamine has n (as an average) equal to at least 10, (for example, as applied to Formula III) to provide better products.

While the value for n as the average number of repeating siloxane units in each occurrence of the polymer used as the gelling agent has been broadly described as 1–300, it is preferred that the value for n be between 10 and 30. Siloxanes with low "n" are relatively expensive, while siloxanes with high "n" (n greater than 30) may be difficult to react.

Illustratively, siloxane/urea copolymers are produced by reacting siloxane diamine with hexamethyldiisocyanate, and then end-capping. The endcapping can, illustratively, be performed using aniline as an endcapper to form phenyl urea end groups; other amino-containing compounds (such as diethyl amine) could also be used as endcappers. In addition alcohols and other suitable reagents may be used. Reaction Scheme II is shown below, to form these copolymers, with the siloxane/urea copolymer shown by the structural Formula II which is then terminated with aniline to produce phenyl urea end groups or hydrolyzed (for example, in the presence of base) to form amine end groups.

Reaction Scheme II

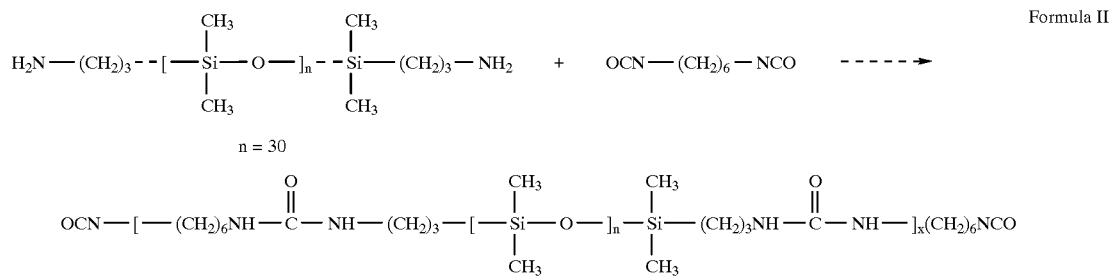

where x has an average value of 1–100 and particularly has a value in the range of 2–40.

This siloxane/urea copolymer of Formula II, then terminated with phenyl urea end groups, softens at 120° C., and about 15% by weight is required to gel cyclomethicone. The gel can be produced by the following procedure: The siloxane/urea copolymer of Formula II, terminated with phenyl urea end groups, and the cyclomethicone are heated above 160° C. and stirred, whereby a clear solution is formed. Gelation occurs on cooling to room temperature; such gels are completely transparent, with their hardness determined by the concentration of polymer. The melting point of the gel is dependent on the concentration of the polymer.

One example of the present invention incorporates polyamides having at least one siloxane group as a vehicle for a solid cosmetic composition, for example, a gel or a stick composition, the vehicle containing a thickening agent and a solvent for the thickening agent, wherein the solvent includes a silicone fluid, and the amide thickening agent includes silicon-containing moieties to enhance compatibility of the silicone fluid in the composition. Embodiments of the present invention also include a solid cosmetic composition containing a cosmetically active ingredient in this vehicle.

An illustrative thickening agent includes, for example, an amide thickening agent which has silicon-containing moieties. According to one aspect of the present invention, such amide thickening agent is a polyamide gelling agent having silicon-containing moieties. Such silicon-modified polyamide can be formed by a copolymerization technique, which involves polymerizing the polyamide from monomers which include a siloxane monomer. For example, the silicon-modified polyamide can be a copolymer which is the product of copolymerization of a dicarboxylic acid with diaminosiloxane oligomers.

Generally, selected copolymers can be produced utilizing the following Reaction Scheme III:

Reaction Scheme III

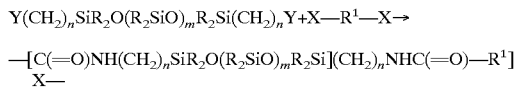

—[C(=O)NH(CH$_2$)$_n$SiR$_2$O(R$_2$SiO)$_m$R$_2$Si](CH$_2$)$_n$NHC(=O)—R$^1$]
X— where:
R at each occurrence is independently selected from the group consisting of methyl, ethyl, propyl, isopropyl and phenyl wherein the phenyl may optionally be substituted by 1–3 members from the group consisting of methyl and ethyl; more particularly R can be methyl, ethyl and phenyl; and especially methyl;

R$^1$ is an alkyl chain having 1–40 carbons, particularly 2–20 carbons and especially 2–6 carbons optionally substituted by a member selected from the group consisting of C1–C4 alkyl, phenyl, hydroxyl, carboxyl and amino and, more particularly, from the group consisting of methyl, ethyl, propyl, isopropyl phenyl, and hydroxyl and optionally containing at least one alkenyl or aromatic group in the main chain or in a pendent group;

X=NH$_2$ when Y=CO$_2$H and X=CO$_2$H when Y=NH$_2$. Thus, as seen in the foregoing reaction, the silicone-containing monomer can be either the diacid or the diamine.

Mixtures of diacids (dicarboxylic acids) as well as mixtures of diamines can be used in the polymerization. Illustrative diacids for making the copolymer include dimer acids (hydrogenated or non-hydrogenated), adipic acid, butanedioic acid, tartaric acid, gluconic acid, oxalic acid, diglycolic acid, malonic acid, succinic acid, glutaric acid, malic acid, maleic acid, dodecanedioic acid, terephthalic acid and isophthalic acid, and mixtures. If a silicon-based dicarboxylic acid is used, a variety of diamines could be used to make the polyamide (for example, ethylene diamine, hexamethylene diamine, piperizine, phenylenediamine, decamethylene diamine, xylene diamine, polyethylene glycol diamine. Also, diamines containing silicone may be used such as those having segments of 1–300 siloxane groups.

Alternatively, the silicon-containing polyamide gelling agent can be produced by silyl amidation of dimer-based polyamides. This approach involves the reaction of free acid sites existing on an original polyamide as terminal sites, with oligosiloxane-amines and/or oligosiloxane-diamines (amidation reaction), or alternatively with oligosiloxane-alcohols or oligosiloxane-diols (esterification reaction). The esterification reaction requires the presence of acid catalysts, as known in the art. It is desired that the polyamide having free acid sites, utilized for the amidation or esterification reaction, have a relatively large number of acid end groups (for example, polyamides with high acid numbers of, for example, 15–20).

For the amidation of free acid sites of polyamides, illustratively (and not to be limiting) siloxane diamines with n (siloxane groups) equal to 1–300, more particularly 2–50 and even more particularly selected from the group consisting of 2, 6, 9.5, 12, 13.5, 23 and 31 can be used for reaction with dimer-based polyamides. The most preferred value for n is 13.5. Best results have been achieved with the siloxane diamine having n=13.5, and with polyamides containing high levels of carboxylic acid end-groups. Reactions were performed either in xylene to extract produced water from the solution by azeotropic distillation, or at higher temperatures (around 180°C.–200° C.) without solvents. Typically, the efficiency of the amidation and reaction rates decrease when the siloxane diamine is longer (higher n). Free amine sites can be capped after the initial amidation reaction of diamino-siloxanes by reacting with either siloxane acid or an organic acid such as benzoic acid.

For the esterification of free acid sites on polyamides, this can be performed in boiling xylene with about 1% by weight (of the total weight of the reaction materials) para toluene sulfonic acid as catalyst.

In the amidation of the free acid sites, cyclomethicone incorporation ability increases as the number of siloxane groups/amide group increases, as shown below in Table 2:

TABLE 2

| siloxane groups/amide group | clear gels with maximum % of cyclomethicone in solvent |
| --- | --- |
| 0 | 40 |
| 0.5 | 55 |
| 1.3 | 55 |
| 2.6 | 59 |

An example of this amidation is shown in the following Reaction Scheme IV:

Reactive Scheme IV

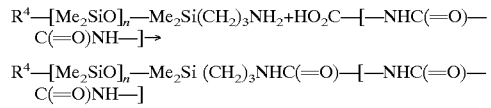

R$^4$—[Me$_2$SiO]$_n$—Me$_2$Si (CH$_2$)$_3$NHC(=O)—[—NHC(=O)—C(=O)NH—]

where R$^4$ is selected from the group consisting of hydrogen, methyl, ethyl, propyl and isopropyl, butyl, and straight chain and branched amino alkyls having 1–4 carbons (particularly aminopropyl); and n (average value) is selected to be 1–40, particularly 1–30, more particularly 1–25, with a particular group being a value selected from the group consisting of 1, 2, 3, 7, and 21; and Me=methyl. The product of this reaction provides a polyamide backbone with siloxane termination sites.

In these reactions, silicone moieties are incorporated only at the chain ends. The resulting polymers have relatively large compatibility with silicone fluids, the enhanced compatibility being greater when the starting (original) polyamides have high acid numbers.

Illustratively, but not by way of limitation, the original polyamide can be a dimer based polyamide hot melt adhesive resin such as Unirez 2973, from Union Camp Corp. This polyamide has 5% to 10% free acid sites.

If siloxane diamines are used (that is, an amidation reaction is used), a free amine group is incorporated into the polymer. This free amine group can be reacted with various organic or silicone-based carboxylic acids (for example, disiloxane-dipropionic acid) to produce another amide bond. It is thought that the final product should not have free amine sites, because these groups may result in lower product stability.

Preferably, the silicone-modified polyamide formed by this silyl amidation is obtained by reacting high acid polyamide with oligosiloxane diamines having an average from 10 to 13 repeating siloxane units. The reactants were refluxed in xylene using a reaction assembly consisting of a azeotropic finger to constantly extract the generated water.

If the original polymer (polyamide) contains free amine sites, rather than free acid sites the siloxane reagent should contain an acid group instead of the amine to enable the amidation reaction.

As a third alternative for providing the silicon-modified polyamide gelling agent, an original polyamide having, for example, an ethylene diamine component is reacted with an oligosiloxane diamine at elevated temperatures (for example, 200° C. to 300° C.) so as to perform transamidation whereby the ethylene diamine component in the original polyamide is replaced by the oligosiloxane diamine. It is preferred that the level of replacement be at most 50%, so as to limit reduction of the gelation capability by the polyamide. Polyamides modified by transamidation in this way exhibit greater compatibility with silicone fluids (for example, clear gel compositions can be produced in which the solvent system is approximately 60% cyclomethicone).

For performing the transamidation, illustratively the original polyamide can be polyamides as described in U.S. Pat. No. 5,500,209, referred to previously, or a polyamide with a high acid number. The transamidation takes place at temperatures above 200° C. When higher temperatures are used, reaction time is very short (for example, 0.5 hours to 300° C). Siloxane diamines with n (number of siloxane groups) from 10 to 15 are most suitable for these reactions. Free amine sites formed during the transamidation can be capped by reaction with either siloxane carboxylic acid or an organic acid such as benzoic acid. Polyamide chains can also be broken during the transamidation. The polymer products obtained are not as hard as those formed by end-site amidation reactions; however, they are less sticky. This reaction is very simple and easily controlled.

A still further alternative approach to form the silicon-modified polyamides is the reaction of polysiloxanes bearing amino or acido alkyl groups which can react with organic acids or amines respectively to provide a polyamidosiloxane, having oligosiloxane groups. Aminopropyl siloxane copolymers, as the original polymer to be reacted with an organic acid, are commercially available. This approach is illustrated in the following Reaction Scheme V:

Reaction Scheme V

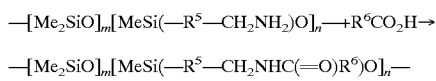

—[Me$_2$SiO]$_m$[MeSi(—R$^5$—CH$_2$NHC(=O)R$^6$)O]$_n$— where:
R$^5$ is selected from the group consisting of —NH—; straight chain and branched C1–C40 alkylenes optionally containing at least one double bond or phenylene group, with particular values for R$^5$ being C1–C20, more particular values being C2–10, and an even more particular value being ethylene;

R$^6$ is selected from the group consisting of C1–C40 aliphatics and phenyl, and more particularly, C1–C10 and phenyl;

n and m are average values and are each independently selected from the range 1–1000, particularly 1–100 and more particularly from 1–50; and Me=methyl. The polymer skeleton in this case is based on siloxane monomeric units and the amide groups are pendant.

In addition to the foregoing, original polyamides (not containing silicon moieties) can be modified, with the modified polyamides utilized in the composition of the present invention as the polyamide gelling agent, by grafting the polyamide with pendant oligosiloxane groups. This can be done in many ways, including (but not limited to):

(a) hydrosilylation of unsaturated bonds in non-hydrogenated dimer-based polyamides;

(b) silylation of the amide groups in polyamides; and (c) silylation of unsaturated polyamides via oxidation.

The substitution by hydrosilylation reaction of unsaturated functional groups found in the polymeric skeleton as integral species of the dimer acid used as the copolymeric unit in the polyamide provides very stable Si—C bonds. This approach is shown by the following Reaction Scheme VI where Polymer C is a dimer based polyamide such as one made with non-hydrogenated dimer acid+ethylene diamine:

Reaction Scheme VI

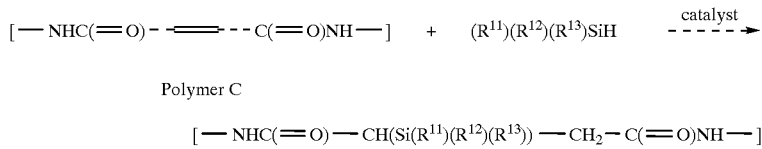

Polymer C

[—NHC(=O)—CH(Si(R$^{11}$)(R$^{12}$)(R$^{13}$))—CH$_2$—C(=O)NH—]

where each of R$^{11}$, R$^{12}$ and R$^{13}$ are independently selected from the group consisting of methyl, ethyl, propyl, isopropyl, butyl, isobutyl, phenyl and a siloxyl group of Formula IV:

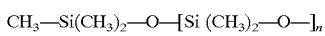

where n is an average and is a number in the range of 1–100.

Examples of suitable values for "(R$^{11}$) (R$^{12}$) (R$^{13}$)SiH" are, illustratively: (CH$_3$)$_3$SiH, (CH$_3$)$_x$Ph$_{3-r}$SiH (where r is a number from 0–3), (CH$_3$)$_3$SiO—[(CH$_3$)$_2$SiO]$_n$—(CH$_3$)$_2$SiH (where n is an 0 average and is a number from 1 to 100), and (CH$_3$)$_r$Bu$_{3-r}$SiH (where Bu is butyl and r is a number from 0–3).

Examples of suitable values for catalysts are organometallic catalysts such as: H$_2$PtCl$_6$, Ru$_3$(CO)$_{12}$, (Ph$_3$P)$_3$RhCl, and others which have the effect of lowering the activation energy of the reaction.

In the present situation (hydrosilylation of unsaturated bonds), as well as in the other reaction schemes described herein, the R groups of the silylated compounds, and the number of substitutions on the polymer, can affect polymer properties (for example, lubricity, crystallinity).

In forming polyamides by hydrosilylation of unsaturated bonds, it is preferred to use original polyamides having higher concentrations of unsaturation. This can accomplished by forming the original polyamide using a highly unsaturated dimer acid, or using various diacids (such as itaconic acid, malic acid, maleic acid, etc.) which contain reactive groups, or by end-capping with an unsaturated mono-acid (such as linoleic acid). In these cases, the polymers are first reacted with siloxane amines or alcohols to eliminate any free acid sites, and then completely dried. After these steps, the hydrosilylation is performed.

As mentioned previously, the silicon-containing polyamide gelling agents utilized in the present invention can be formed by silylation of amide groups in original polyamides. This provides substitution on the amide functional sites. This substitution on the amide functional sites is by catalytic reaction between an hydrido substituted silane ("SiH")and the amide, which can lead to the formation of three potential substituted arrangements, as shown in the following Reaction Scheme VII:

Reaction Scheme VII

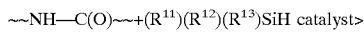

gives the following possible products at that reaction site: —NH—CH(O—Si($R^{11}$) ($R^{12}$) ($R^{13}$))—; —C(O)N—Si—($R^{11}$)($R^{12}$)($R^{13}$)—; and —N=C (O—Si($R^{11}$)($R^{12}$)($R^{13}$))—.

While silylation of the amide groups improves compatibility with the silicone oils, destruction of the amide groups reduces gellation capabilities.

In addition, the silicon-modified polyamides can be formed by silylation of unsaturated polyamides via oxidation. That is, the unsaturated groups can be oxidized to alcohols or diols and then the newly developed hydroxyl groups can be reacted with either siloxane carboxylic acids or siloxane alcohols. Alternatively, the olefinic sites of the unsaturated polyamides can be epoxidized, followed by typical epoxy-ring opening with siloxane amines or siloxane alcohols.

In a series of preferred embodiments base compositions and cosmetic compositions according to the present invention contain a sufficient amount of the thickening agent such that the final cosmetic composition is a solid composition, for example, a gel or stick.

The composition according to the present invention can include other ingredients conventionally incorporated in solid cosmetic compositions, for example, deodorant or antiperspirant gels and/or sticks, particularly if clarity is not a factor. These other ingredients could include an active phase (which may include water or glycol), waxes, other thickeners, surfactants, stabilizers, color and fragrance. As for various other ingredients which can be incorporated, attention is directed to the optional components such as hardeners, strengtheners, chelating agents, colorants, perfumes, emulsifiers and fillers, described in the various patent documents listed in the following, all incorporated by reference herein in their entirety:

U.S. Pat. No. 3,255,082 to Barton;

U.S. Pat. No. 4,049,792 to Elsanu;

U.S. Pat. No. 4,137,306 to Rubino, et al.; and

U.S. Pat. No. 4,279,658 to Hooper, et al.

Attention is also directed to U.S. Pat. No. 5,500,209 for various optional components, and amounts thereof, which can be incorporated in the composition of the present invention.

The degree of freedom in incorporating optional ingredients is increased where a clear composition is not being formed (for example, where a translucent composition, or, especially, where an opaque composition, is being formed).

Base compositions according to the present invention can be made by mixing the various components at an elevated temperature (that is, by heating and mixing the various components) and then cooling in order to form the gelled (solidified) composition, for example, as a gel or stick. For cosmetic compositions, the additional ingredients are added using techniques and at times in the manufacturing process as are known to those in the art. Desirably, any volatile components (such as fragrances) are added to the mixture at a relatively late stage of the mixing, so as to limit volatilization of the volatile components.

Generally, the solvent and thickening agent (for example, the polyamide gelling agent) are mixed and heated so as to fully dissolve the thickening agent in the solvent. An active ingredient (for example, antiperspirant active material, for example, in dry form or as part of a solution) can be added after the thickening agent fully dissolves, and mixing then takes place. Mixing continues with cooling, with, for example, colorant and fragrance then being added. Thereafter, the resulting composition, still liquid, is poured into canisters, for example, dispensing packages, and solidified, as with conventional stick and gel compositions.

The compositions according to the present invention may be used in the same manner as conventional gel or stick compositions, dispensed from, for example, dispensing containers. For example, the gel or stick, exposed out of the dispensing package, is rubbed on skin, so as to deposit the active material (for example, antiperspirant and/or deodorant active materials) on the skin.

Illustratively, where a composition is an antiperspirant composition containing an antiperspirant active material for reducing perspiration in the axillary regions, and exposed portion of the composition is rubbed against axillary regions of the human body, so as to deposit the antiperspirant active material and, if present, deodorant active material, on the skin in the axillary region. The composition, both during the deposition on the skin and after application, has reduced tackiness and stickiness, as discussed previously.

In the following, illustrative contemplated examples of compositions within the scope of the present invention are set forth. These contemplated examples are illustrative of the present invention, and are not limiting. Amounts of components in these examples are in weight percent, of the total weight of the composition.

Compositions according to the present invention can be made by the following procedure. This procedure is illustrative and not limiting of the present invention. The polymer can be dissolved in the silicone fluid, for example, at elevated temperatures (for example, up to 160° C.) so as to form a solution, with cooling then being performed to form the gel. It is preferred that the solution is not heated too long or at too high a temperature, since such disadvantageously may cause the gel to be colored (rather than clear and colorless). The cosmetic active can be added to the solution of silicone fluid and polymer gelling agent and mixed therewith so as to be homogeneously distributed in the product.

The cosmetic composition according to the present invention can be packaged in conventional containers, using conventional techniques. For example, where the composition is a stick composition, the composition, while still in liquid form, can be introduced into a dispensing package as conventionally done in the art, and cooled therein so as to thicken in the package. Where a gel or soft-solid cosmetic composition is produced, the composition can be introduced into a dispensing package (for example, a package having a top surface with slots or pores) as conventionally done in the art. Thereafter, the product can be dispensed from the dispensing package as conventionally done in the art, to deposit the active material, for example, on the skin. This provides good deposition of the active material on the skin.

For example, where the product is a solid stick product, the product can be elevated out of the dispensing package so as to expose an end of the stick, which exposed end can then be rubbed on the skin to deposit the composition, including active material, on the skin. Where the product is a gel or soft-solid, the product can be dispensed by extruding the product from the dispensing package onto the top surface of the package, through pores or slots in the top surface, and then rubbing the exposed product on the skin so as to deposit the active material on the skin.

In the following, specific synthesis examples for forming siloxane polymers having hydrogen-bonding groups are set forth, and specific examples of compositions within the scope of the present invention are set forth. These specific synthesis examples and examples are illustrative in connection with the present invention, and are not limiting. In the following, as well as throughout the present disclosure, names utilized are the CTFA (Cosmetics, Toiletry and Fragrance Association, Inc.) names, as set forth in the *CTFA International Cosmetic Ingredient Dictionary* (4th Ed. 1991), the contents of which dictionary are incorporated herein by reference in their entirety.

SYNTHESIS EXAMPLE 1

A main-chain siloxane-urea copolymer is synthesized in tetrahydrofuran (THF) as solvent. A solution of 1 molar part of hexamethylene diisocyanate is added dropwise to a solution of 1 molar part of a liquid telechelic diamino siloxane (molar mass: 2500 g/mol.). The solution becomes viscous at the end of the addition. After the polymerization the solvent is removed by evaporation, a clear and colorless polymer is obtained (molar mass: 31030 g/mol; molecular weight distribution: 1.9; determined by gel permeation chromatography (GPC) (polystyrene standard)).

COPOLYMER OF SYNTHESIS EXAMPLE I

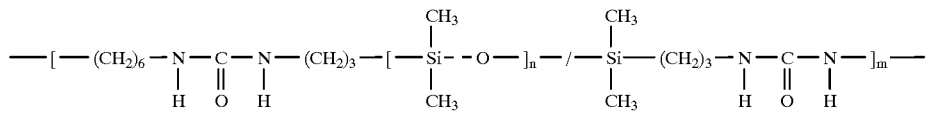

where n has an average value of 1–30 and m has an average value of 1–12, and wherein the polymer can contain various n and m units each of which can have a different number and may be randomly arranged.

SYNTHESIS EXAMPLE 2

A main-chain siloxane-urea copolymer is synthesized in THF as solvent. A solution of 1 molar part of isophorone diisocyanate is added dropwise to a solution of 1 molar part of a liquid telechelic diamino siloxane (molar mass: 2500 g.mol). (Note: A polymer can be considered telechelic if it contains end groups that react selectively to give a bond with another molecule, including for chain extension by means of bifunctional linking agents. Telechelic materials can be called macromolecular monomers, macro monomers, or macromers, or reactive oligomers and contain repeating units such as $z^1$—$(A)_n$—$Z^2$ where $Z^1$ and $Z^2$ are reactive acids, A=a chain for example, containing aliphatic and/or aromatic units or siloxane units), and n>1. More concisely, they are molecules which have reactive ends and which contain repeating units in the molecule. The solution becomes viscous at the end of the addition. After the polymerization the solvent is removed by evaporation. The resulting polymer is dissolved in THF and diethyl amine is added. After the reaction the solvent is removed by evaporation, yielding a clear and colorless polymer (molar mass: 50090 g/mol.; molecular weight distribution: 2.2; determined by GPC (polystyrene standard)).

COPOLYMER OF SYNTHESIS EXAMPLE 2:

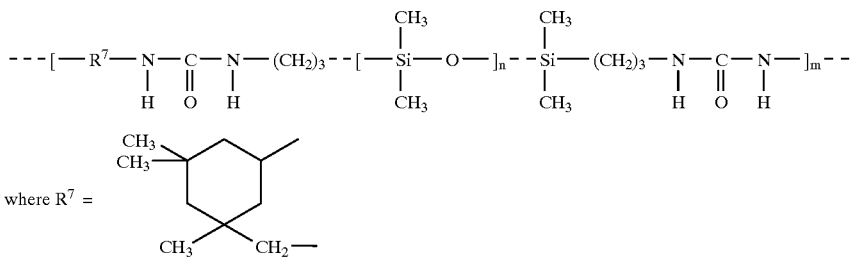

n has an average value of 30 and m has an average value of 19, and wherein the polymer can contain various n and m units each of which can have a different number and may be randomly arranged. Note that in other embodiments of this copolymer n may be selected to be in the range of 1–303, particularly 1–100, more particularly 1–30, and may be selected to be in the range of 1–19.

SYNTHESIS EXAMPLE 3

A main-chain siloxane-urea copolymer is synthesized in cyclomethicone (Dow Corning 245 fluid). 1 molar part of hexamethylene diisocyanate is dispersed in Dow Corning 245 fluid at room temperature. It is not soluble in the solvent at room temperature. The mixture is heated up to 90° C. The mixture becomes homogeneous. Now a solution of 1 molar part of a telechelic diamino siloxane (molar mass: 2500 g/mol) is added dropwise. The solution becomes viscous at the end of the addition. By cooling down the gelation take place by the interaction of hydrogen bonds with cooling (molar mass of the polymer: 18600 g/mol; molecular weight distribution: 2.2; determined by GPC (polystyrene standard)).

COPOLYMER OF SYNTHESIS EXAMPLE 3:

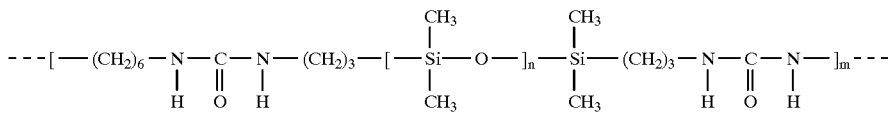

n has an average value of 30 and m has an average value of 7, and wherein the polymer can contain various n and m units each of which can have a different number and may be randomly arranged. Note that in other embodiments of this copolymer n may be selected to be in the range of 1–300, particularly 1–100 and more particularly 1–30; and m may be selected to be in the range of 1–100, particularly 1–19 and more particularly 1–7.

This synthesis shows that the siloxane polymer can be directly formed in the silicone fluid. This avoids the need to evaporate the solvent in which the siloxane polymer is formed.

SYNTHESIS EXAMPLE 4

A main-chain siloxane-urea copolymer is synthesized in THF as solvent. A solution of 0.75 molar part of a liquid telechelic diamino siloxane (molar mass: 2500 g/mol) is added dropwise to a solution of 1 molar part of hexamethylene diisocyanate. A solution of 0.25 molar part of a second diamine, a mixture of 2,2,4-trimethyl 1,6-diamino hexane and 2,4,4-trimethyl 1,6-diamino hexane (molar ratio: 1:1), is added in the same manner. After the polymerization the solvent is removed by evaporation, yielding a clear and colorless polymer (molar mass: 35040 g/mol; molecular weight distribution: 1.5, determined by GPC (polystyrene standard)).

wherein m has an average value of 13; n has an average value of 30; and o has an average value of 4; and the portions designated in brackets with m and o can occur as block or random segments in the polymer chain. Note that in other embodiments of this copolymer m may be selected to be in the range of 1–100, particularly 1–20 and more particularly 3–19; n may be selected to be in the range of 1–300, particularly 1–100 and more particularly 30–60; and o may be selected to be in the range of 1–100, particularly 1–20 and more particularly 3–7.

This synthesis example shows use of a plurality of diamine monomers, including the diamine siloxane, in forming the siloxane polymer. The plurality of monomers can modify properties of the gel (for example, provide a gel with higher gel point, provide a less elastic and softer gel, etc.).

SYNTHESIS EXAMPLE 5

A main-chain siloxane-urea copolymer is synthesized in THF as solvent. A solution of 0.66 molar part of a liquid telechelic diamino siloxane (molar mass: 5000 g/mol) is added dropwise to a solution of 1 molar part of hexamethylene diisocyanate. A solution of 0.33 molar part of a second telechelic siloxane diamine (molar mass: 2500 g/mol) is added in the same manner. After the polymerization the solvent is removed by evaporating, yielding a clear and colorless polymer (molar mass: 88400 g/mol; molecular weight distribution: 1.9; determined by GPC (polystyrene standard)).

COPOLYMER OF SYNTHESIS EXAMPLE 4:

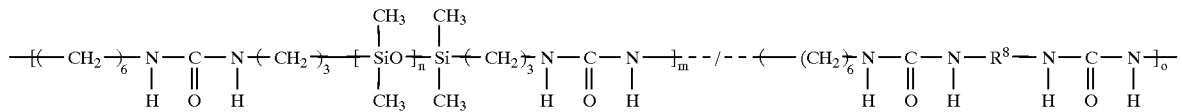

wherein each occurrence of $R^8$ is independently selected from the group consisting of:

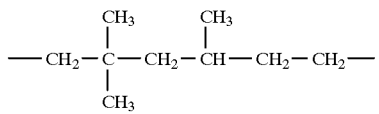

and

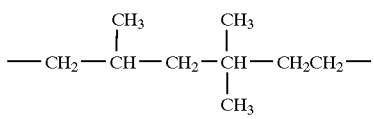

COPOLYMER OF SYNTHESIS EXAMPLE 5:

wherein m has an average value of 14; n has an average value of 60; o has an average value of 30; and p has an average value of 7; and the portions designated in brackets with m and p can occur as block or random segments in the polymer chain. Note that in other embodiments of this copolymer m may be selected to be in the range of 1–100, particularly 1–20 and more particularly 3–19; n may be selected to be in the range of 1–300, particularly 1–100 and more particularly 30–60; o may be selected to be in the range of 1–300, particularly 1–100 and more particularly 30–60; and p may be selected to be in the range of 1–300, particularly 1–100 and more particularly 30–60.

SYNTHESIS EXAMPLE 6

A main-chain siloxane-urea copolymer synthesized in THF as solvent. A solution of 0.66 molar part of a liquid telechelic diamino siloxane (molar mass: 5000 g/mol) is added dropwise to a solution of 1 molar part of hexamethylene diisocyanate. A solution of 0.33 molar part of a second telechelic siloxane diamine (molar mass: 1000 g/mol) is added in the same manner. After the polymerization the solvent is removed by evaporating. The resulting polymer was dissolved in THF and diethyl amine is added. After the reaction the solvent is removed by evaporating, yielding a clear and colorless polymer (molar mass: 48670 g/mol; molecular weight distribution: 1.7; determined by GPC (polystyrene standard)).

COPOLYMER OF SYNTHESIS EXAMPLE 6:

wherein: m has an average value of 9; n has an average value of 30; o has an average value of 10; and p has an average value of 4; and the portions designated in brackets with m and p can occur as block or random segments in the polymer chain, and the ends may be terminated with a group such as (O)=C—N(CH$_2$CH$_3$)$_2$. Note that in other embodiments of this copolymer m may be selected to be in the range of 1–100, particularly 1–20 and mor particularly 3–19; n may be selected to be in the range of 1–300, particularly 1–100 and more particularly 30–60; o may be selected to be in the range of 1–300, particularly 1–100 and more particularly 30–60; and p may be selected to be in the range of 1–300, particularly 1–100 and more particularly 30–60.

SYNTHESIS EXAMPLE 7

A main-chain siloxane-urea-urethane "Copolymer VII" is synthesized in THF as solvent. A solution of 0.25 molar part of 1,4-benzenedimethanol together with dibutyl tin dilaurate is added dropwise to a solution of 1 molar part of hexamethylene diisocyanate. Then the solution is heated up to 67° C. for 3 hours. A solution of 0.75 molar part of a liquid telechelic diamino siloxane (molar mass 2500 g/mol) is added in the same manner. After the polymerization, the solvent is removed by evaporation, yielding a clear and colorless polymer. Polymer mass: 48,030 g/mol; molecular weight distribution: 3.0; determined by GPC (polystyrene standard.

COPOLYMER OF SYNTHESIS EXAMPLE 7 ("Colpolymer VII"):

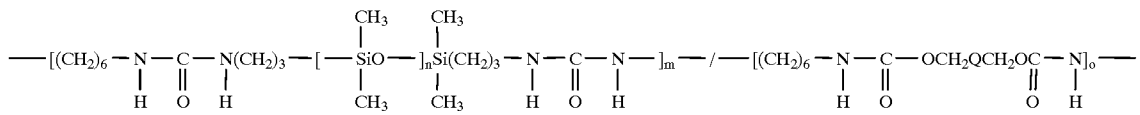

wherein:
Q=phenyl; m has an average value of 17; n has an average value of 30; o has an average value of 6; and the portions designated in brackets with m and o can occur as block or random segments in the polymer chain. Note that in other embodiments of this copolymer m may be selected to be in the range of 1–100, particularly 1–20 and mor particularly 3–19; n may be selected to be in the range of 1–300, particularly 1–100 and more particularly 30–60; and o may be selected to be in the range of 1–100, particularly 1–20 and more particularly 3–7.

SYNTHESIS EXAMPLE 8

A main-chain siloxane-urea-urethane "Copolymer VIII" is synthesized in THF as solvent. A solution of 0.75 molar part of a liquid telechelic diamino siloxane (molar mass: 2500 g/mol) is added dropwise to a solution of 1 molar part of hexamethylene diisocyanate. A solution of 0.25 molar part of polyethylene glycol (molar mass: 600 g/mol) together with dibutyl tin laurate is added in the same manner. Then the solution is heated up to 67° C. for 3 hours. After the polymerization, the solvent is removed by evaporation, yielding a clear and colorless polymer.

COPOLYMER OF SYNTHESIS EXAMPLE 8
("COPOLYMER VIII"):

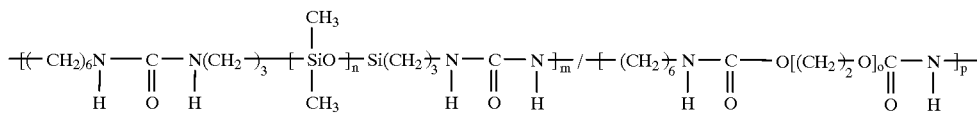

wherein:

m has an average value of 10; n has an average value of 30; o has an average value of 25 and p has an average value of 4; and the portions designated in brackets with m and p can occur as block or random segments in the polymer chain. Note that in other embodiments of this copolymer m may be selected to be in the range of 1–100, particularly 1–20 and mor particularly 3–19; n may be selected to be in the range of 1–300, particularly 1–100 and more particularly 30–60; o may be selected to be in the range of 1–1000, particularly 1–100, more particularly 1–30 and especially 25; and p may be selected to be in the range of 1–100, particularly 1–20 and more particularly 3–7.

SYNTHESIS EXAMPLE 9

A pendant-chain siloxane-urea polymer is synthesized in THF as solvent. A solution of 1 molar part of phenylene isocyanate is added dropwise to a solution of 0.5 molar part amino groups of a liquid siloxane (molar mass: 2900 g/mol, 7 mol % of amino groups.) The liquid siloxane was AMS-162 from Gelest, Inc. (Tullytown, Pa.), an aminopropyl/methylsiloxane-dimethylsiloxane copolymer with 80–100 cP viscosity. The solution becomes viscous at the end of the addition. The reaction continues for 2 hours at room temperature. After the reaction the solvent is removed by evaporating, yielding a yellow polymer (molar mass: 6600 g/mol; molecular weight distribution: 1.6; determined by GPC (polystyrene standard)). The polymer produced was a comb-branch urea molecule, of the type depicted in FIG. 4.

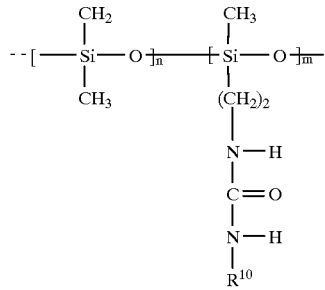

where $R^{10}$=phenyl and n is selected to give the molecular mass of 6600 g/mol. Note that in other embodiments of this copolymer m may be selected to be in the range of 1–300, particularly 1–100 and more particularly 30–60; and n may be selected to be in the range of 1–300, particularly 1–100 and more particularly 30–60.

SYNTHESIS EXAMPLE 10

A tetraterminated siloxane-urea polymer is synthesized in dioxane as solvent. A solution of 1.5 molar part of phenylene isocyanate is added dropwise to a solution of 1.0 molar part amino groups of a liquid siloxane (molar mass: 900 g/mol. 4 amino groups per chain). The solution becomes viscous at the end of the addition. After the reaction the solvent is removed by evaporation, yielding a yellow polymer (molar mass: 3900 g/mol; molecular weight distribution: 8.6; determined by GPC (polystyrene standard)).

POLYMER SYNTHESIS EXAMPLE 10

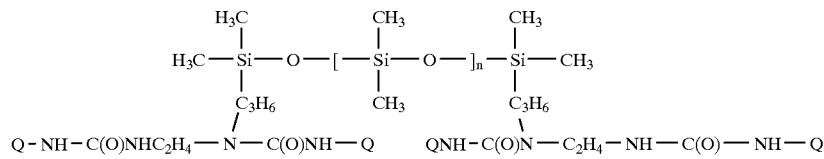

where Q=phenyl and each Q is attached to a nitrogen (shown) and n is selected to give a molecular mass of 3900 g/mol. Note that in other embodiments of this copolymer n may be selected to be in the range of 1–300, particularly 1–100 and more particularly 30–60.

SYNTHESIS EXAMPLE 11:

A main-chain siloxane-urea-urethane "Copolymer XI" is synthesized in THF as solvent. A solution of 0.5 molar part of a liquid telechelic diamino siloxane (molar mass 2500 g/mol) is added dropwise to a solution of 1.0 molar part of hexamethylene diisocyanate. A solution of 0.5 molar part of a liquid telechelic hydroxy-terminated siloxane (molar mass: 4200 g/mol) together with dibutyl tin dilaurate is added in the same manner. Then the solution is heated up to 67° C. for 12 hours. After the polymerization, the solvent is removed by evaporation, yielding a clear and colorless polymer. Molar mass: 19,340 g/mol; molecular weight distribution: 1.6; determined by GPC (polystyrene standard.

COPOLYMER OF SYNTHESIS EXAMPLE 11 ("COPOLYMER XI"):

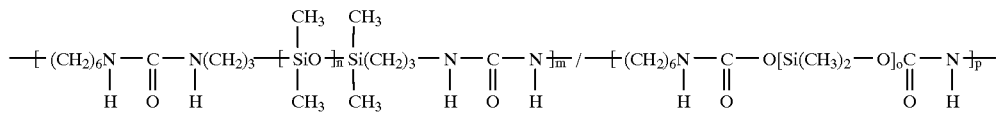

wherein:

m has an average value of 3; n has an average value of 30; o has an average value of 57 and p has an average value of 3; and the portions designated in brackets with m and p can occur as block or random segments in the polymer chain. Note that in other embodiments of this copolymer m may be selected to be in the range of 1–100, particularly 1–20 and more particularly 1–5; n may be selected to be in the range of 1–300, particularly 1–100 and more particularly 10–60; o may be selected to be in the range of 1–300, particularly 1–100 and more particularly 10–60; and p may be selected to be in the range of 1–100, particularly 1–20 and more particularly 1–5.

In the following examples, as well as throughout the present specification, various names utilized are the CTFA (Cosmetics, Toiletries and Fragrance Association, Inc.) names, as set for in the CTFA International Cosmetic Ingredient Dictionary (4th Ed. 1991).

The following Table 3 shows specific silicon-modified polyamide gellants and amide was co-gellants. Examples 1, 4 and 5 are Examples of the current invention. Examples 2 and 3 form amide wax co-gellants and are the subject of a separate co-pending application.

TABLE 3

| Example | Reagent (gm/gm of PA) | Catalyst or Additive Quantity | Extent of Reaction[a] (%) | Siloxane Units per Amide (molar units) |
|---|---|---|---|---|
| 1 | $HSi(CH_3)_2OSi(CH_3)_3$/ 0.30 g | $Ru_3(CO)_{12}$/5 mg | 3.2 | 0.06 |
| 2 | $[H_2N(CH_2)_3Si(CH_3)_2]_2O$ (0.5 g)[b] | stearic acid | 84.7 | 0.85 |
| 3 | $[H_2N(CH_2)_3Si(CH_3)_2]_2O$ (0.5 g)[b] | acetic acid | 91.6 | 0.92 |
| 4 | $HSi(CH_3)_2OSi(CH_3)_3$/ (0.88 g) | $Ru_3(CO)_{12}$/15 mg | 35.1 | 0.70 |
| 5 | $[H_2N(CH_2)_3Si(CH_3)_2O Si(CH_3)_2]_2O$/ (0.5 g) |  | 4.3 | 0.17 |

[a]mole % of additive calculated based on the NMR integration comparison between the $Si(CH_3)$ group and —$CH_3$ group of the PA.
[b]mol ratio relative to counter acid.

Table 4 shows formulations of Examples 1–5 from Table 3 in various solutions. In Table 4, C-41 is Ceraphyl 41 and, together with the cyclomethicone, is a solvent for the formulations shown. One (1) gram of each formulation was used, except for those in a formulation weight ratio of "(0.5/1.0)", which contained 1.5 grams of the formulation. In these examples, the polyamide (PA) used was Unirez, a product of Union Camp Corp.

TABLE 4

| Formulation[a] (includes polyamide or wax of specified Example of Table 3) | C-41 (gm) | Cyclomethicone (gm) | Observation |
|---|---|---|---|
| Ex. 1 | 5.4 | 5.4 | clear gel |
| Ex. 1 | 5.4 | 6.0 | slightly cloudy |
| Ex. 1 | 6.0 | 6.0 | almost clear |
| Ex. 4/PA[b] (0.5/0.5) | 5.4 | 5.0 | clear gel |
| Ex. 4/PA (0.5/0.5) | 6.0 | 6.0 | very slightly cloudy |
| Ex. 2/PA (0.5/0.5) | 5.4 | 6.5 | almost clear; hard |
| Ex. 2/PA (0.5/1.0) | 8.5 | 9.5 | almost clear; hard |
| Ex. 2/PA (0.5/0.5) | 4.5 | 5.3 | clear; hard |
| Ex. 3/PA (0.5/1.0) | 5.4 | 6.0 | slightly cloudy after 2 mos. |
| Ex. 5 | 5.4 | 6.0 | clear |
| Ex. 5 | 5.4 | 6.5 | slightly cloudy |

[a]Weight ratios
[b]PA = "Unirez 2973"

Thus, according to the present invention, a solid (for example, gel or stick) composition, having enhanced compatibility with silicone fluids, is provided. The compositions can provide clear cosmetic (for example, antiperspirant and/or deodorant) compositions, utilizing a polyamide gelling agent, while providing a composition having improved application and cosmetic properites, including reduced tackiness and stickiness.

Formulations which could be used to form actual products are shown as follows. A composition of the invention may be substituted for the term "silicon-modified polyamide (gellant)".

FORMULATION EXAMPLES

Example 1

The polymer used (denoted Gellant A in the following) is similar to Example 4, above, except that the molar ratio is 3/1 instead of 1/1. This copolymer is a polysiloxane-urea copolymer polymerized from hexamethylene diisocyanate and a molar ratio of 3/1 of (1) DMS-A15 (a siloxane diamine with average n~30) and (2) 2,2(4),4-trimethyl 1,6-diamino hexane.

Gellant A: 20%
Cyclomethicone: 69% (mixture of Dow Corning 245 and 345 fluids)
Isocetyl alcohol: 10%
Fragrance: 1%

This formulation is a clear deodorant stick with good payout.

Example 2

The polymer used (designated Gellant B in the following) is structural Formula (I) set forth previously.

Gellant B: 32%
Cyclomethicone (Dow Corning 345 fluid): 67%
Fragrance: 1%

This formulation is a clear deodorant gel.

Example 3

The polymer used (denoted Gellant C in the following) is structural Formula (II) terminated with phenyl urea end groups, set forth previously.

Gellant C: 24.4%
Cyclomethicone (Dow Corning 246 fluid): 27.3%
Isocetyl alcohol: 9.8%
Sorbitan Oleate (Arlacel 80, a surfactant): 4.9%
Antiperspirant active (Rezal 36GP): 19.5%
Distilled water: 14.1%

The procedure for forming this formulation follows: the polymer, cyclomethicone and isocetyl alcohol were mixed with heating until a clear, homogeneous liquid solution was produced. The Arlacel 80 and Rezal 36GP were added, with vigorous stirring. Then water was added slowly. This produced a non-tacky, opaque antiperspirant cream.

Example 4

Product of Synthesis Example 9: 47.7%
Cyclomethicone (Dow Corning 245 fluid): 51.3%
Fragrance: 1%

All components were mixed with heating until a clear solution formed. On cooling, a slightly yellow, clear deodorant gel was produced.

AMIDE EXAMPLES

The following examples show formulations suitable for use with amides, but ureas and urethanes of this invention may also be used in such formulations in place of "silicon-modified polyamide (gellant)".

| 1) | Deodorant stick | |
|---|---|---|
| | silicon-modified polyamide (gellant) | 12% |
| | C12–15 alkyl lactate (Ceraphyl 41) (emollient) | 35% |
| | cyclomethicone (silicone fluid) | 52% |
| | fragrance (deodorant active) | 1% |
| 2) | Antiperspirant stick | |
| | silicon-modified polyamide (gellant) | 12% |
| | aluminum chlorohydrate (antiperspirant active) | 25% |
| | cyclomethicone (silicone fluid) | 35% |
| | C12–15 alkyl lactate (Ceraphyl 41) (emollient) | 28% |
| 3) | Deodorant gel | |
| | silicon-modified polyamide (gellant) | 6% |
| | C12–15 alkyl lactate (Ceraphyl 41) (emollient) | 38% |
| | cyclomethicone (silicone fluid) | 55% |
| | fragrance (deodorant active) | 1% |

Thus, according to the present invention, a base composition, which is a thickened composition, thickened to be a gel, soft-solid or stick, and which can contain increased levels of silicone fluids, can be achieved. This composition can also include cosmetically active materials, including antiperspirant and/or deodorant active materials, so as to provide cosmetic compositions, including deodorant and/or antiperspirant compositions for reducing body malodor. Base compositions and cosmetic compositions can be provided as clear and transparent compositions, having good cosmetic properties, particularly in view of the large amounts of silicone fluids that can be incorporated therein. As an antiperspirant composition, the composition has high efficacy, an attractive appearance and leaves substantially no visible (white) residue either upon application or after drying of the composition.

While we have shown and described several embodiments in accordance with the present invention, it is understood that the same is not limited thereto or the specific embodiments described herein, but is susceptible to numerous changes and modifications as known to one having ordinary skill in the art, and we therefore do not wish to be limited to the details shown and described herein, but intend to cover all such modification as are encompassed by the scope of the appended claims.

We claim:

1. A base composition suitable for use in forming a cosmetic composition wherein said base composition comprises:
   (a) a fluid component comprising at least one silicone fluid;
   (b) at least one gelling agent in a type and amount sufficient to thicken the fluid component wherein said gelling agent is selected from the group consisting of polymers which:
      (1) contain both siloxane groups and hydrogen-bonding groups to thicken base compositions containing volatile and/or non-volatile silicone fluids, wherein (i) each segment of siloxane units in the polymer contains an average of from 1–1000 siloxane units and (ii) the hydrogen bonding groups are selected from the group consisting of ester groups, urethane groups, urea groups, thiourea groups, amide groups and combinations of the foregoing;
      (2) a renon-flowable at room temperature; and
      (3) are dissolvable in the fluid component at a temperature of 25–250 degrees C to form a translucent or clear solution at a temperature in the range of 25–250 degrees C.

2. A composition according to claim 1 wherein each segment of siloxane units in the polymer contains an average of from 1–300 siloxane units.

3. A composition according to claim 2 wherein each segment of siloxane units in the polymer contains an average of from 10–100 siloxane units.

4. A composition according to claim 1 wherein the polymers dissolve in a fluid which contains silicone which fluid is at a temperature of less than 200 degrees C.

5. A composition according to claim 1 wherein the silicone fluid is cyclomethicone.

6. A composition according to claim 2 wherein the silicone fluid is cyclomethicone.

7. A composition according to claim 1 further comprising a cosmetically active ingredient selected from the group consisting of fragrances, sunscreens, antiperspirants, deodorants and antibacterials.

8. A composition according to claim 7 wherein the composition is an antiperspirant composition.

9. A composition according to claim 8 wherein the antiperspirant is selected from the group comprising aluminum chlorohydrate, aluminum chloride, aluminum sesquichlorohydrate, aluminum chlorohydrex PG, aluminum chlorohydrex PEG, aluminum dichlorohydrex PG, aluminum dichlorohydrex PEG, zirconyl hydroxychloride, nitradohydrate and aluminum-zirconium glycine complexes.

10. A composition according to claim 9 wherein the aluminum-zirconium glycine complex is selected from the group consisting of aluminum zirconium tetrachlorohydrex gly, aluminum zirconium trichlorohydrex gly, aluminum zirconium pentachlorohydrex gly, and aluminum zirconium octochlorohydrex gly.

11. A composition according to claim 8 wherein the antiperspirant is included in the composition in a solution comprising at least one of water and propylene glycol.

12. A composition according to claim 8 wherein the cosmetic composition is a stick antiperspirant composition.

13. A composition according to claim 8 wherein the cosmetic compositon is a gel antiperspirant composition.

14. A composition according to claim 1 wherein a clear solution is formed.

15. A composition according to claim 2 wherein a clear solution is formed.

16. A composition according to claim 14 wherein the siloxane is selected from the group consisting of phenyl trimethicone and cyclic dimethyl siloxanes.

17. A composition according to claim 1 wherein the silicone fluid is selected from the group consisting of:
(a) linear siloxanes optionally containing aromatic substitution; and
(b) cyclic siloxanes having from 4–6 members in a ring optionally substituted by C1–C6 alkyl or phenyl.

18. A composition according to claim 1 wherein the gelling agent is added in an amount of 1–60 percent by weight.

19. A composition according to claim 18 wherein the gelling agent is added in an amount of 5–30 percent by weight.

20. A composition according to claim 19 wherein the gelling agent is added in an amount of 10–20 percent by weight.

21. A composition according to claim 1 wherein the silicone fluid is added in an amount of 0.5–95 percent by weight.

22. A composition according to claim 21 wherein the silicone fluid is added in an amount of 10–80 percent by weight.

23. A composition according to claim 22 wherein the silicone fluid is added in an amount of 20–75 percent by weight.

24. A composition according to claim 23 wherein the silicone fluid is added in an amount of 30–70 percent by weight.

25. A composition according to claim 1 wherein the gelling agent added does not exceed 50 percent by weight of the base composition.

26. A composition according to claim 2 wherein the gelling agent added does not exceed 50 percent by weight of the base composition.

27. A composition according to claim 1 comprising at least 50 percent by weight of a silicone oil.

28. A composition according to claim 1 further comprising additional solvents selected from the group consisting of solvents which are themselves miscible in the silicon fluid and mixtures of solvents which as a mixture are miscible in the silicone fluid.

29. A composition according to claim 2 further comprising additional solvents selected from the group consisting of solvents which are themselves miscible in the silicon fluid and mixtures of solvents which as a mixture are miscible in the silicon fluid.

30. A composition according to claim 1 further comprising at least one additional ingredient suitable for forming a cosmetic composition, wherein the at least one additional ingredient is added in an amount of 0.5–85 percent by weight based on the weight of the base composition as 100 percent.

31. A composition according to claim 1 further comprising at least one additional ingredient suitable for forming a cosmetic composition, wherein the at least one additional ingredient is an antiperspirant and is added in an amount of 0.5–85 percent by weight based on the weight of the base composition as 100 percent.

32. A composition according to claim 31 wherein the amount of additional ingredient is 1–75 percent.

33. A composition according to claim 32 wherein the amount of additional ingredient is 2–55 percent.

34. A composition according to claim 31 comprising at least one surfactant.

35. A composition according to claim 34 comprising at least one surfactant selected from the group consisting of alkanolamides, ethoxylated amides, amine oxides, ethoxylated carboxylic acids, ethoxylated glycerides, glycol esters, monoglycerides, polyglyceryl esters, polyhydric alcohol esters, polyhydric alcohol ethers, sorbitan/sorbitan esters, triesters of phosphoric acid, ethoxylated alcohols, ethoxylated lanolin, ethoxylated polysiloxanes, propoxylated polyoxyethylene ethers and alkylpolyglycosides.

36. A composition according to claim 31 comprising a surfactant selected from the group consisting of nonionic surfactants and blends of nonionic surfactants with cationic or anionic surfactants.

37. A composition according to claim 31 wherein the surfactant is selected from the group consisting of N-alkyl pyrrolidone, the polyethylene glycol amide of tallow acid that conforms generally to the formula RC(O)—NH—(CH$_2$CH$_2$O)$_n$H where RCO— represents the fatty acids derived from tallow and n has an average value of 50, cocamidopropylamine oxide, the polyethylene glycol diester of lauric acid that conforms generally to the formula CH$_3$(CH$_2$)$_{10}$C(O)—(OCH$_2$CH$_2$)$_n$O—C(O)(CH$_2$)$_{10}$CH$_3$, a polyethylene glycol derivative of Castor Oil with an average of 4 moles of ethylene oxide, propylene glycol ricinoleate, glycerol myristate, polyglyceryl-4 oleyl ether, sucrose distearate, sorbitan sesquiisostearate, trioleth-8 phosphate, laureth-4, a polyethylene glycol derivative of Lanolin with an average of 20 moles of ethylene oxide, dimethicone copolyol, the polyoxypropylene, polyoxyethylene ether of cetyl alcohol that conforms generally to the formula $CH_3(CH_2)_{14}CH_2(OCH(CH_3)CH_2)_x(OCH_2CH_2)_yOH$ where x has an average value of 5 and y has an average value of 20, and lauryl glucose.

38. A composition according to claim 31 wherein the surfactant is selected from the group consisting of N-alkyl pyrrolidone, the polyethylene glycol amide of tallow acid that conforms generally to the formula $RC(O)-NH-(CH_2CH_2O)_nH$ where RCO— represents the fatty acids derived from tallow and n has an average value of 50, cocamidopropylamine oxide, the polyethylene glycol diester of lauric acid that conforms generally to the formula $CH_3(CH_2)_{10}(O)-(OCH_2CH_2)_nO-C(O)(CH_2)_{10}CH_3$, a polyethylene glycol derivative of Castor Oil with an average of 4 moles of ethylene oxide, propylene glycol ricinoleate, glycerol myristate, polyglyceryl-4 oleyl ether, sucrose distearate, sorbitan sesquiisostearate, trioleth-8 phosphate, laureth-4, a polyethylene glycol derivative of Lanolin with an average of 20 moles of ethylene oxide, dimethicone copolyol, the polyoxypropylene, polyoxyethylene ether of cetyl alcohol that conforms generally to the formula $CH_3(CH_2)_{14}CH_2(OCH(CH_3)CH_2)_x(OCH_2CH_2)_yOH$ where x has an average value of 5 and y has an average value of 20, and lauryl glucose.

39. A composition according to claim 31 wherein the surfactant is present in an amount of 0–15 percent by weight.

40. A composition according to claim 31 wherein the surfactant is present in an amount of 0–4 percent by weight.

41. A composition according to claim 11 wherein the composition is a multiphase system.

42. A composition according to claim 41 wherein the gelling agent comprises at least one polyamide group.

43. A composition according to claim 41 wherein the composition is a stick, gel or cream.

44. A composition according to claim 1 wherein the hydrogen bonding group is selected from the groups consisting of urea, urethane and amide.

45. A composition according to claim 1 comprising a multiphase system.

46. A composition according to claim 1 in which the cosmetic composition formed with the base composition is selected from the group consisting of a cream, gel and stick.

47. A composition according to claim 1 wherein the polymer is selected from the group consisting of siloxane/urea copolymers which are linear and which contain urea groups as hydrogen-bonding groups in the backbone of the polymer.

48. A composition according to claim 1 wherein the polymer is a polysiloxane terminated with four urea groups represented by Formula I:

$$HN(Ph)-C(O)-HN-C_2H_4-N(C(O)N(Ph)H)-\underset{C_3H_6}{\underset{|}{Si(CH_3)}}-O-[\underset{CH_3}{\underset{|}{Si(CH_3)}}-O-]_n-\underset{C_3H_6}{\underset{|}{Si(CH_3)}}-CH_3, \quad N(C(O)N(Ph)H)-C_2H_4-NHC(O)N(Ph)H$$

where Ph=phenyl and n is an average number for the number of dimethyl siloxane units and n is an average number and is selected from 0–300.

49. The composition according to claim 48 wherein n represents an average value and is a number from 0–100.

50. The composition according to claim 49 wherein n is 50.

51. A composition according to claim 1 wherein said gelling agent is endcapped.

52. A composition according to claim 51 wherein said end capping is effected with the use of an agent selected from the group consisting of C1–C20 aliphatic monohydric alcohols, C1–C6 aliphatic amines, phenyl amine optionally substituted by 1–3 members selected from C1–C20 aliphatics, C1–C20 aliphatic acids and C1–C20 aliphatic acid chlorides.

53. A composition according to claim 52 wherein said end capping is effected with aniline.

54. A composition according to claim 51 wherein end capping is effected by hydrolysis to form an amine end group.

55. A composition according to claim 1 wherein the polymer is an end-capped siloxane/urea copolymer of Formula II:

$$OCN-[(CH_2)_6NH-\overset{O}{\overset{\|}{C}}-NH-(CH_2)_3-[Si(CH_3)_2-O]_n-Si(CH_3)_2-(CH_2)_3NH-\overset{O}{\overset{\|}{C}}-NH]_x-(CH_2)_6NCO$$

where x is an average and is a number in the range of 1–100.

56. A composition according to claim 55 wherein x=2–40.

57. A composition according to claim 1 wherein the polymer is a main-chain siloxane-urea copolymer of the following formula:

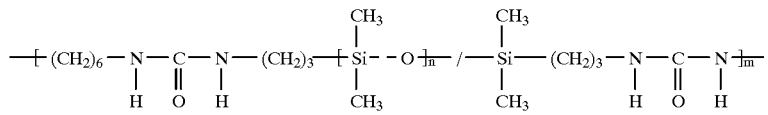

where n has an average value of 1–30 and m has an average value of 1–12, and wherein the polymer can contain various n and m units each of which can have a different number and may be randomly arranged.

58. A composition according to claim 1 wherein the polymer is a main-chain siloxane-urea copolymer of the following formula:

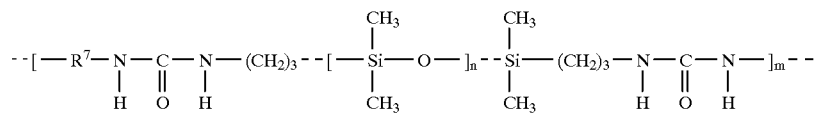

where n has an average value in the range 1–300, 1–100 or 1–30 and m has an average value in the range of 1–100 or 1–19, and wherein the polymer can contain various n and m units each of which can have a different number and may be randomly arranged.

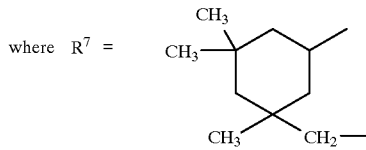

59. A composition according to claim 1 wherein the polymer is a main-chain siloxane-urea copolymer of the following formula:

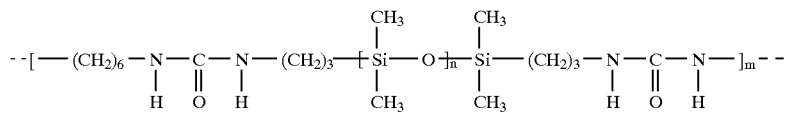

where n has an average value in the range of 1–300, 1–100 or 1–30 and m has an average value in the range of 1–100, 1–19 or 1–7, and wherein the polymer can contain various n and m units each of which can have a different number and may be randomly arranged.

60. A composition according to claim 1 wherein the polymer is a main-chain siloxane-urea copolymer of the following formula:

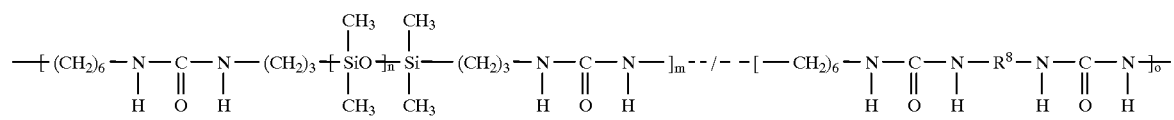

wherein each occurrence of $R^8$ is independently selected from

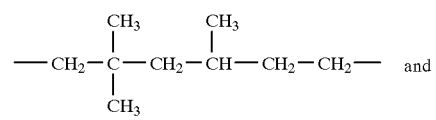

-continued

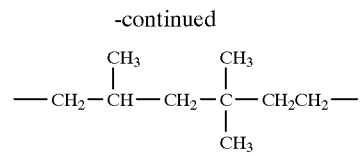

where m has an average value of 1–100, 1–20 or 3–19; n has an average value of 1–300, 1–100 or 30–60; o has an average value of 1–100, 1–20 or 3–7; and the portions designated in brackets with m and o can occur as block or random segments in the polymer chain.

61. A composition according to claim 1 wherein the polymer is a main-chain siloxane-urea copolymer of the following formula:

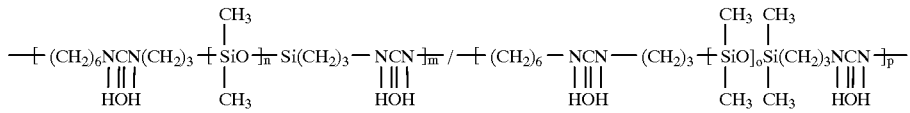

where n has an average value of 1–300, 1–100 or 30–60; m has an average value of 1–100, 1–20 or 3–19; o has an average value of 1–300, 1–100 or 30–60; p has an average value of 1–300, 1–100 or 30–60; and the portions designated in brackets with m and p can occur as block or random segments in the polymer chain.

62. A composition according to claim 1 wherein the polymer is a main-chain siloxane-urea copolymer of the following formula:

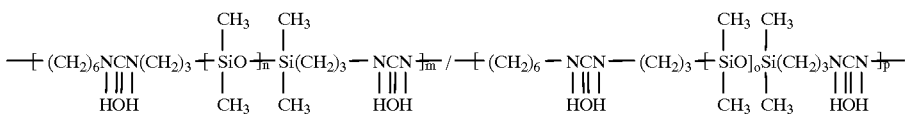

where n has an average value of 1–300, 1–100 or 30–60; m has an average value of 1–100, 1–20 or 3–19; o has an average value of 1–300, 1–100 or 30–60; p has an average value of 1–300, 1–100 or 30–60; the portions designated in brackets with m and p can occur as block or random segments in the polymer chain; and the ends may be terminated with (O)=C—N(CH$_2$CH$_3$)$_2$.

63. A composition according to claim 1 wherein the polymer is a main-chain siloxane-urea-urethane copolymer of the following formula:

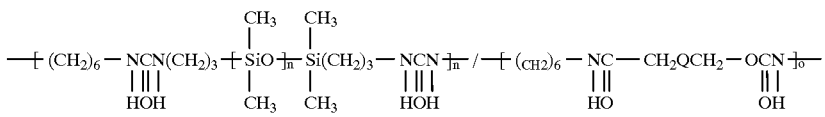

where Q=phenyl, m has an average value in the range of 1–100, 1–20 or 3–19; n has an average value in the range of 1–300, 1–100 or 30–60; o has an average value in the range of 1–100, 1–20 or 3–7; and the portions designated in brackets with m and o can occur as block or random segments in the polymer chain.

64. A composition according to claim 1 wherein the polymer is a main-chain siloxane-urea-urethane copolymer of the following formula:

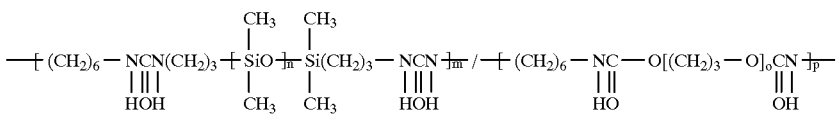

where n has an average value of 1–300, 1–100 or 30–60; m has an average value of 1–100, 1–20 or 3–19; o has an average value of 1–1000, 1–100, 1–30 or 25; p has an average value of 11–100, 1–20 or 3–7; and the portions designated in brackets with m and p can occur as block or random segments in the polymer chain.

65. A composition according to claim 1 wherein the polymer is a comb-branch pendant-chain siloxane-urea polymer having segments of the following formula:

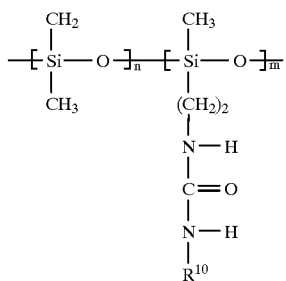

where $R^{10}$=phenyl; n has an average value of 1–300, 1–100 or 30–60 and m has an average value of 1–300, 1–100 or 30–60.

66. A composition according to claim 1 wherein the polymer is a tetra-terminated siloxane-urea polymer having segments of the following formula:

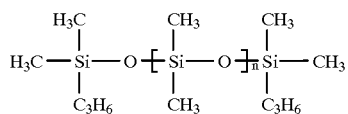

where Q=phenyl and n has an average value of 1–300, 1–100 or 30–60.

67. A composition according to claim 1 wherein the polymer has the following formula

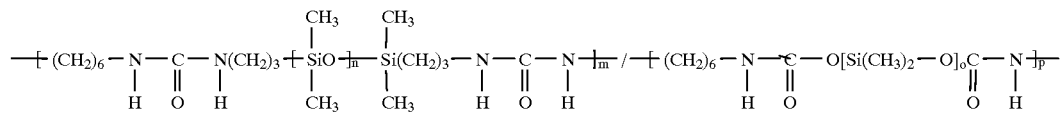

wherein:
m has an average value in the range of 1–100, 1–20 or 1–5; n has an average value in the range of 1–300, 1–100 or 10–60; o has an average value in the range of 1–300, 1–100 or 10–60; and p has an average value in the range of 1–100, 1–20 or 1–5, and the portions designated in brackets with m and p can occur as block or random segments in the polymer chain.

68. A composition according to claim 67 in which the siloxane polymers are formed by reacting a member of the group consisting of siloxane diacids and siloxane acid derivatives with a member of the group consisting of diols and diamines.

69. A composition according to claim 67 wherein a polymer comprising a polyamide without silicon moieties is modified by grafting the polyamide with pendant oligosiloxane groups using a method selected from the group consisting of:
(a) hydrosilation of unsaturated bonds in non-hydrogenated dimer-based polyamides;
(b) silylation of the amide groups in polyamides; and
(c) silylation of unsaturated polyamides by oxidation.

70. A composition according to claim 1 wherein the gelling agent is a polyamide.

71. A composition according to claim 1 wherein the gelling agent comprises siloxane copolymers in which a siloxane diamine is reacted with a diacid, diacid derivative, diisocyanate or diisothiocyanate.

72. A composition according to claim 1 wherein the gelling agent comprises siloxane copolymers produced by Reaction Scheme III:

Reaction Scheme III

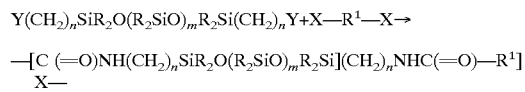

where:
R at each occurrence is independently selected from the group consisting of methyl, ethyl, propyl, isopropyl and phenyl wherein the phenyl may optionally be substituted by 1–3 of a member of the group consisting of methyl and ethyl;
$R^1$ is an alkyl chain selected from the group consisting of 1–40 carbons, 2–20 carbons and 2–6 carbons and optionally substituted by a member selected from the group consisting of C1–C4 alkyl, phenyl, hydroxyl, carboxyl and amino and optionally containing at least one alkenyl or aromatic group in the main chain or in a pendent group; and
X=$NH_2$ when Y=$CO_2H$ and X=$CO_2H$ when Y=$NH_2$.

73. A base composition suitable for use in forming a cosmetic composition wherein said base composition is made by combining in any order:
(a) a fluid component comprising at least one silicone fluid;
(b) at least one gelling agent in a type and amount sufficient to thicken the fluid component wherein said gelling agent is selected from the group consisting of polymers which:
(1) contain both siloxane groups and hydrogen-bonding groups to thicken base compositions containing volatile and/or non-volatile silicone fluids, wherein (i) each segment of siloxane units in the polymer contains an average number of siloxane units n wherein n is a number from 1–1000; and (ii) the hydrogen bonding groups are selected from the group consisting of ester groups, urethane groups, urea groups, thiourea groups, amide groups and combinations of the foregoing;
(2) are non-flowable at room temperature; and
(3) are dissolvable in the fluid component at a temperature of 25–250 degrees C to form a translucent or clear solution at a temperature in the range of 25–250 degrees C.

74. A composition according to claim 1 wherein the composition includes the addition of a cosmetically active ingredient selected from the group consisting of fragrances, sunscreens, antiperspirants, deodorants and antibacterials.

75. A cosmetic composition for reducing malodor of a human person which composition comprises a composition made according to claim 5.

76. A cosmetic composition for reducing malodor of a human person which composition comprises a composition made according to claim 14.

77. A cosmetic composition for reducing malodor of a human person which composition comprises a composition made according to claim 29.

78. A cosmetic composition for reducing malodor of a human person which composition comprises a composition made according to claim 31.

79. A cosmetic composition for reducing malodor of a human person which composition comprises a composition made according to claim 73.

80. A composition according to claim 73 wherein n is a number from 1–300.

81. A composition according to claim 80 wherein n is a number from 1–100.

* * * * *